| United States Patent [19]
Tanida et al.

[11] B 3,989,685
[45] Nov. 2, 1976

[54] PROCESS FOR MAKING A 2'-HALOPENICILLIN

[75] Inventors: Hiroshi Tanida, Osaka; Teruji Tsuji, Takatsuki, both of Japan

[73] Assignee: Shinogi & Co., Ltd., Japan

[22] Filed: June 21, 1973

[21] Appl. No.: 372,016

[44] Published under the second Trial Voluntary Protest Program on March 9, 1976 as document No. B 372,016.

[30] Foreign Application Priority Data

June 29, 1972 Japan.............................. 47-65355
Nov. 14, 1972 Japan............................ 47-114105

[52] U.S. Cl.......................... 260/239.1; 260/243 C; 424/244

[51] Int. Cl.²...................................... C07D 499/04

[58] Field of Search.................................. 260/239.1

*Primary Examiner*—Richard J. Gallagher
*Assistant Examiner*—Jose Tovar
*Attorney, Agent, or Firm*—Wenderoth, Lind & Ponack

[57] ABSTRACT

A 2'-halopenicillin compound is prepared from a penicillin-1-oxide compound by the action of an acid halide in the presence of a base. The product on heating rearranges to a 3-halo-3-methylcepham compound which itself gives a 3-methyl-3-cephem compound on further heating. A 2'-halopenicillin compound gives a 3-methyl-3-cephem compound on heating. The 2'-halopenicillin compounds, 3-halo-3-methylcepham compound and 3-methyl-3-cephem compounds are antibacterials which are also useful as intermediates for the synthesis of other penicillins and cephalosporins.

7 Claims, No Drawings

PROCESS FOR MAKING A 2'-HALOPENICILLIN

This invention relates to a process for the preparation of new 2'-halopenicillin compounds (Compound II), 3-halo-3-methylcepham compounds (Compound III), the products of these reactions; and to a new process for the preparation of 3-methyl-3-cephem compounds (Compound IV).

The inventors found that treatment of a penicillin-1-oxide compound (I) with an organic acid halide in the presence of a base gives a 2'-halopenicillin compound (II) as a sole isolated product, and that when warmed in a solution, 2'-halopenicillin compound II transformed into a 3-halo-3-methylcepham compound (III) as a result of rearrangement, and the product III was then led to a 3-methyl-3-cephem compound (IV) by further thermal treatment eliminating hydrogen halide. It was also found that when prolonged thermal treatment was carried out, Compound II directly converted to Compound IV. Related reactions reported in literatures include the reaction of Compound I with acid anhydrides in the absence of base to give a mixture of 2'-acetoxypenicillins, 3-acetoxy-3-methylcephams, and 3-methyl-3-cephems (Journal of the American Chemical Society, Vol. 91, page 1401 (1969)), the reaction of Compound I with thionyl chloride in the presence of triethylamine to give a mixture of Compounds II, III, and IV (Journal of the American Chemical Society, Vol. 94, 7169 (1972)), and the reaction of Compound I with pyridine-hydrochloric acid salt to yield Compounds II, III, $\Delta^2$-isomer of III, and IV. (Netherlands Patent Application No. 72.08671). The latter two reactions were reported after the priority date of our invention. However, the formation of only one product in the present invention, and of the mixtures in the reported reactions strongly implies that the underlying reaction mechanisms are different. Our invention seems us superior over the reported reactions in the exclusive transformation and high yield of 2'-halopenicillinscompounds (II) and Compounds III and IV, which are promissing material for the synthesis of other useful penicillins and cephalosporins. The sulfoxides of the 2'-halopenicillin compounds (II) and of the 3-halo-3-methylcepham compounds (III) were obtained by the action of conventional oxidizing reagents for sulfoxide formation, on the corresponding Compounds II and III.

The reactions of our invention are shown in the following scheme:

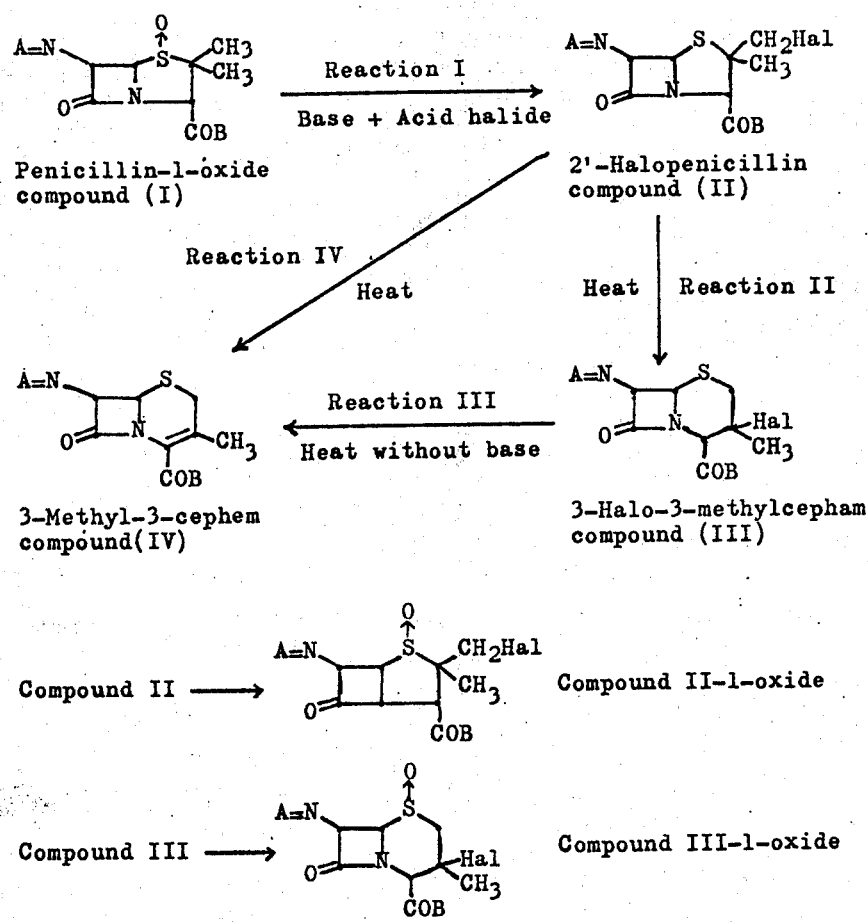

wherein A is two hydrogens or an amino-substituent; B is a hydroxy or a carboxy-protecting group; and Hal is a halogen.

The structural formulae in this specification include every stereo-isomer represented by the formulae. When B is a hydroxy, it can form salts, which can also be deemed as carboxy-protecting groups, or as equivalents of hydroxy interconvertible in solution. The term lower means having 1 - 12 carbon atoms.

(EXPLANATION OF SYMBOLS)

A. Hal groups: The halogen represented by Hal in the formulae is fluorine, chlorine, bromine, or iodine, among which chlorine is the most preferable for this invention.

B. A groups: A represents two hydrogens or an amino-substituent, in which the amino-substituent can be a hydrogen and a mono-valent amino-substituent, two mono-valent amino-substituents, or a di-valent amino-substituent. Representative amino-substituents are a lower hydrocarbon group, an inorganic acyl group, organic acyl group, and tri-lower alkylsilyl group.

Representative mono-valent lower hydrocarbon groups include a lower alkyl (e.g. methyl, ethyl, propyl, isobutyl, tert-butyl, octyl, adamantyl, hydroxymethyl, phenoxymethyl, methoxymethyl), lower unsaturated hydrocarbon group (e.g. vinyl, ethynyl, 2-propinyl, 1-carbethoxy-1-propen-2-yl, cyclohexenyl, tetrahydropyranyl), five or six-membered cyclic, mono-, or bicyclic, carbo- or one to five-nitrogen-, oxygen- and/or sulfur-hetero-cyclic, lower aromatic group (e.g. phenyl, naphthyl, pyrimidyl), lower aralkyl (e.g. benzyl, benzhydryl, trityl, phenethyl, 2-pyridylmethyl, triazolylethyl), and the like groups. Representative di-valent lower hydrocarbon groups include a lower alkylidene (e.g. ethylidene, isopropylidene, dialkylaminomethylene, cyclohexylidene), lower aralkylidene (e.g. benzylidene, naphthylmethylidene, furfuridene), and the like groups. These mono- or di-valent lower hydrocarbon groups can be unsaturated or substituted by a substituent linked through carbon (e.g. lower alkyl, lower aryl, lower aralkyl), oxygen (e.g. hydroxy, lower alkoxy, lower acyloxy), sulfur (e.g. lower alkylthio, lower arylthio, lower acylthio, mercapto), nitrogen (e.g. amino, lower alkylamino, nitro), or by a halogen. The substituted groups are useful when the substitution renders the group easy to remove (e.g. an alkyl or aralkyl substituted by α-hydroxy, lower alkoxy, substituted amino, carboxy, or carbalkoxy, or by β-oxo, thioxo, nitro, or halogen), or when the substitution make the compounds pharmaceutically favourable.

Representative mono-valent inorganic acyl groups include a substituted carbonic acyl (e.g. lower alkoxycarbonyl, lower aralkoxycarbonyl, carbamoyl, thiocarbamoyl, N-lower alkylcarbamoyl), substituted sulfuric acyl (e.g. lower alkoxysulfonyl, sulfamyl, lower alkylsulfamyl), substituted phosphoric acyl (e.g. lower alkylphosphoryl, amidophosphoryl, phenylphosphoryl), and like groups. Representative di-valent inorganic acyl groups include a carbonyl, lower alkylaminomethoxymethylidene, and the like.

The organic acyl groups are acyl groups derived from a lower carboxylic, sulfonic, sulfenic, or phosphonic, or like acids. Some compounds having there groups show strong antibacterial activity.

Representative mono-valent organic acyl groups include a sulfonic acyl group ($RSO_2$-), sulfenic acyl group (RS-), phosphonic acyl group (R-$PO_2$-), and carboxylic acyl group (RCO-), in which R is a hydrogen or an organic group optionally substituted by an oxygen, sulfur, nitrogen, or carbon functions, halogen, or other substituent.

Some of the pharmacologically preferable acyl groups are represented by the following formula:

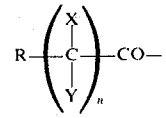

wherein $n$ is zero or one; and R is a hydrogen or a hydrocarbon group, for example, a straight, branched, or cyclic lower alkyl (e.g. methyl, ethyl, propyl, butyl, pentyl, heptyl, isobutyl, cyclopentyl, cyclohexyl, norbornyl, adamantyl); lower aralkyl (e.g. benzyl, naphthylmethyl, benzhydryl, trityl); or five or six-membered cyclic, mono- or bi-cyclic, carbo- or one to five nitrogen-, oxygen-, and/or sulfur-hetero-cyclic lower aryl (e.g. phenyl, naphthyl, tetrahydronaphthyl, furyl, thienyl, thiazolyl, oxazolyl, imidazolyl, triazolyl, tetrazolyl, oxadiazolyl, pyridyl, tetrahydrofuranyl). These groups can be unsaturated or substituted by an oxygen function (e.g. hydroxy, lower alkoxy, lower aryloxy, lower acyloxy, oxo), sulfur function (e.g. mercapto, lower alkylthio, lower arylthio, lower acylthio, lower sulfonyl, sulfo, thioxo), nitrogen function (e.g. amino, substituted amino, cyano, azido, hydroxyimino, nitro), halogen (e.g. fluorine, chlorine, bromine, iodine), or a carbon function (e.g. lower alkyl, five or six-membered cyclic, mono- or bi-cyclic, carbo- or one to five nitrogen, oxygen and/or sulfur hetero-cyclic aryl, lower aralkyl, lower acyl, carboxy, formyl, substituted carboxy). X is a hydrogen or an oxygen function (e.g. hydroxy, lower alkoxy, lower aryloxy, lower acyloxy, or together with Y, an oxo), sulfur function (e.g. mercapto, lower alkylthio, lower arylthio, lower acylthio, sulfo, or, together with Y, an thioxo), nitrogen function (e.g. amino, lower hydrocarbylamino, lower acylamino, azido, nitro), halogen (e.g. fluorine, chlorine, bromine, iodine), or a carbon function (e.g. lower alkyl, lower alkenyl, lower cycloalkyl optionally unsaturated, five or six-membered cyclic, mono- or bi-cyclic, carbon or one to five-nitrogen, oxygen, and/or sulfur heterocyclic lower aryl, lower aralkyl optionally substituted, carboxy optionally in the form of an ester, amide or salt, nitrile). Y is a hydrogen or one of the groups cited for the groups R and X. Y and R or X can be combined to form a cyclic group.

Specific examples of these acyl groups are a lower alkanoyl (e.g. formyl, acetyl, propionyl, butyryl, hexanoyl, octanoyl, cyclopentanecarbonyl, cyclohexanepropionyl, 1-adamantoyl); unsaturated lower aliphatic carboxylic acyl (e.g. acryl, crotonyl, 3-butenoyl, 3-pentenoyl, 2-hexenoyl); lower aliphatic carboxylic acyl substituted by an oxygen function (e.g. methoxyacetyl, ethoxypropionyl, hemisuccinyl, carbomethoxyacetyl, carbamoylacetyl, phenoxyacetyl, phenoxypropionyl, phenoxybutyryl, benzyloxyacetyl); lower aliphatic carboxylic acyl substituted by a sulfur function (e.g. methylthioacetyl, butylthioacetyl, allylthioacetyl, phenylthioacetyl); lower aliphatic carboxylic acyl substituted by a nitrogen function (e.g. glycyl, azidoacetyl, cyanoacetyl, cyanopropionyl, 5-amino-5-carboxypentanoyl, 1-amino-cyclopentanecarbonyl, 2-aminoindane-2-carbonyl); lower aliphatic carboxylic acyl substituted by halogen (e.g. chloroacetyl, bromoacetyl, dichloroacetyl, α-halovaleryl); lower aralkyl carboxylic acyl (e.g. phenylacetyl, 4-hydroxyphenylacetyl, 3-chlorophenylacetyl, 4-aminomethylphenylacetyl, furylacetyl, thienylacetyl, 1-methyl-5-tetrazolylacetyl, 1-tetrazolylacetyl, 4-isothiazolylacetyl); lower aralkyl carboxylic acyl substituted by an oxygen, carbon, sulfur, or nitrogen function or halogen (e.g. α-hydroxyphenylacetyl, α-lower alkanoyloxyphenylacetyl, α-lower alkoxyphenylacetyl, α-carboxyphenylacetyl, α-carboxythienylacetyl, α-carboxypyridylacetyl, α-methylthiophenylacetyl, 4-pyridylthioacetyl, N-methylpyridinium-4-thioacetyl, α-sulfophenylacetyl, α-sulfothienylacetyl, phenylglycyl, p-hydroxyphenylglycyl, 4-hydroxy-3-chlorophenylglycyl, N-sulfophenylglycyl, N-guanidinocarbamoylthienylglycyl, cyclohexadienylglycyl, thienylglycyl, α-halophenylacetyl); and mono- or bi-cyclic, five or six-membered cyclic, carbo- or one to five-nitrogen, oxygen, and/or sulfur hetero-cyclic aromatic lower carboxylic acyl (e.g. benzoyl, o-carboxybenzoyl, 2,6-dimethoxybenzoyl, tetrahydronaphthalenecarbonyl, 2-lower alkoxy-1-naphthalenecarbonyl, 3-phenyl-5-methylisoxazolyl-4-carbonyl, 3-(2,6-dichlorophenyl)-5-methylisoxazol-4-ylcarbonyl, 1-phenylpyrazolyl-3-carbonyl, nicotinoyl, furoyl, thienylcarbonyl). These acyl groups can be unsaturated or be substituted by an oxygen, sulfur, nitrogen, and/or carbon function, halogen, or other substituents as cited above.

The reactive groups can be protected by conventional methods prior to the reactions, the protecting group being eliminated after the reaction. For example, a hydroxygroup hydroxy group be protected as an ester, enol-ether, or ketal, and deprotected with an acid or base. An amino group can be protected by e.g. 2,2,2-trichloroethoxycarbonyl or 2-haloethoxycarbonyl, and the protecting group removed by reductive hydrolysis; or it can be protected with e.g. phenacyloxycarbonyl, tert-butoxycarbonyl, N-alkylcarbamoyl, trityl, 1-carbethoxypropen-2-yl, or 1-carbamoylpropen-2-yl, and the protecting group removed by hydrolysis with an acid or base. A carboxy group can be protected in the forms of e.g. a salt, ester, halide, or anhydride.

These mono-valent acyl groups can be removed by conventional methods in the art as described below.

Representative di-valent organic acyl groups include oxaloyl, succinyl, maleoyl, phthaloyl, 2-sulfonylbenzoyl, pyridine-2,3-dicarbonyl, and other aliphatic or aromatic di-valent acyl groups forming an imide group when combined with the nitrogen in the group A=N. These groups can be removed by conventional methods e.g. by the action of hydrazine.

The group A can also be a mono-valent acyl group and a mino-valent group e.g. lower hydrocarbon group or tri-lower alkylsilyl group, for example, together with nitrogen of A=N forming 4-oxo-5-phenyl-3-imidazolidinyl, 2,2-dimethyl-4-oxo-5-phenyl-3-imidazolidinyl, 5-cyclohexadienyl-2,2-dimethyl-4-oxo-3-imidazolidinyl, 2,2-dimethyl-4-oxo-1-nitroso-5-phenyl-3-imidazolidinyl; these being pharmacologically favourable groups. The group A can also be two mono-valent acyl groups.

C. B groups: B is a hydroxy or a carboxy-protecting group. The carboxy-protecting group, taken together with the adjacent CO group, include an ester, anhydride, or salt when B is an oxygen function; and amide, imide, or azide when B is a nitrogen function; and a thiol ester or thiol acid when B is a sulfur function.

Representative esters includes esters with a lower aliphatic alcohol (e.g. methyl, ethyl, propyl, tert-butyl, vinyl, propargyl esters), esters with an aromatic hydroxy compound (e.g. phenyl, naphthyl, and pyridyl esters), esters with a lower aralkyl alcohol (e.g. benzyl, benzhydryl, and trityl esters), an ester with hydroxylamine, and the like; representative salts include alkali metal salts, alkaline earth metal salts, silyl esters, tin esters, organic base salts, and the like. Representative amides include unsubstituted amides, and substituted amides (e.g. N-methylamide, N-phenylamide, hydroxyamide); representative imides include o-sulfobenzoylimide, and the like. The ester, amide, and imide groups stated above can be substituted by any substituent e.g. a carbon function (e.g. lower alkyl, lower acyl, lower aryl), nitrogen function (e.g. optionally substituted amino, nitro), oxygen function (e.g. hydroxy, lower alkoxy, lower acyloxy, lower aryloxy, carbolower alkoxy), and/or halogen, or the like groups.

An easily removable group is especially useful for the production of antibacterial substances. Typical examples of such groups includes a halo-lower alkyl ester (e.g. 2-chloro-ethyl, 2-bromoethyl, 2-iodoethyl, 2,2,2-trichloroethyl esters), lower acyl-lower alkyl ester (e.g. lower alkanoylemethyl, 2-acetylethyl, phenacyl, p-bromophenacyl, 2-benzoylethyl, α-benzoylbenzyl, tosylmethyl, 2-tosylethyl esters), lower alkoxy-lower alkyl ester (e.g. methoxymethyl ester), lower acyloxy-lower alkyl ester (e.g. acetoxymethyl, pivaloyloxymethyl, N,N-dimethylglycyloxymethyl, benzoyloxymethyl esters), lower 1,1-dicarbo-lower alkoxyalkyl ester (e.g. dicarbomethoxymethyl, dicarbethoxymethyl esters), lower aryl ester (e.g. phenyl, naphthyl, pyridyl esters optionally substituted by e.g. nitro, methoxy, or lower alkyl), aralkyl ester (e.g. benzyl, benzhydryl, trityl, naphthylmethyl, and pyridylmethyl esters, optionally substituted by e.g. lower alkyl, hydroxy, lower alkoxy, nitro, halogen, lower alkylthio, or the like), ester with a hydroxylamine (e.g. optionally substituted isopropylideneamino, benzalimino esters), amide (e.g. amide, N-methoxyamide, hydroxyamide, imide with saccharin), salt (e.g. trimethylsilyl, pentamethyldisilyl, trimethyltin salts, alkali metal salts, alkaline earth metal salts, or organic base salts), and other conventional carboxy-protecting groups.

Some of the esters show strong antibacterial activity. Representative of these are 1-lower acyloxy-1-lower alkyl esters and 1-lower alkoxy-lower alkyl esters as stated above; methyl ester, N,N-dimethylaminoethyl ester, O-ester of benzaldoxime, and phenacyl esters.

The carboxy-protecting groups can be removed by a conventional method in the art, for example, by hydrolysis with acid or base, reductive fission, and photochemical fission, as described below.

COMPOUNDS

The compounds of this invention are represented by a general formula

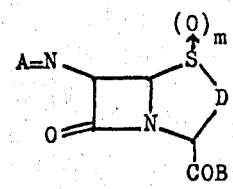

wherein A is two hydrogens or amino-substituent, B is a hydroxy or carboxy-protecting group, D is a

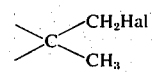

or

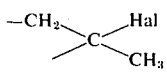

group in which Hal is a halogen, and *m* is zero or one. The groups A and B are shown above in the item of explanation of symbols. Important groups A include that consisting of a hydrogen and an acyl group of the formula

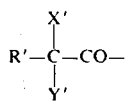

wherein R' is a hydrogen or a lower alkyl group, a lower cycloalkyl group, a lower aralkyl group, or mono- or bi-cyclic, five or six-membered cyclic, a carbo- or one to five-nitrogen, oxygen, and/or sulfur-hetero-cyclic lower aryl group, which are, where possible optionally unsaturated or substituted by an oxygen, sulfur, nitrogen, and/or carbon function, or a halogen; X' is a hydrogen or an oxygen, sulfur, nitrogen, or carbon function or halogen, or R', C and X' combined together represents a lower alicyclic group; and Y' is a hydrogen or a group cited for R' or X'. Preferable group of these include a group of formula

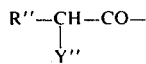

wherein R'' is a hydrogen, a lower alkyl group, a cyano group, or a mono-cyclic, carbo- or one to five-nitrogen, oxygen, and/or sulfur-hetero-cyclic lower aryl group, and Y'' is a hydrogen or a lower alkanoyloxy; lower aryloxy; hydroxy; amino optionally protected by a lower alkoxycarbonyl; lower alkylthio; amidinothio; lower arylthio; lower aralkylthio; lower alkyl; or combined with R'' and C forms a lower alicyclic group. These can be unsaturated or substituted, where possible, by a nitrogen, oxygen, sulfur, or carbon function, and/or halogen. Typical example of these are phenoxyacetyl, phenylacetyl, thienylacetyl, phenylgycyl optionally substituted by a lower alkoxycarbonyl group, 2-ketopinoyl, or norbornanecarbonyl group.

Other type of important amino-substituents include that consisting of a hydrogen and a mono- or bi-cyclic, five or six-membered cyclic, carbo- or one to five nitrogen, oxygen, and/or sulfur hetero-cyclic aromatic mono-valent carboxylic acyl; carbonic acyl; sulfonic acyl; sulfenic acyl; lower alkyl; lower alkylidene; or lower aralkylidene, all of them can be unsaturated or substituted, where possible, by a halogen or a lower alkyl, lower aryl, lower aralkyl, hydroxy, lower alkoxy, lower acyloxy, amino, lower alkylamino, lower acylamino, nitro, and/or lower alkylthio; and that combined with the nitrogen of A=N group to form imide, i.e. bivalent lower carboxylic acyl of lower aliphatic mono-cyclic, carbo- or one to five-nitrogen, oxygen, and/or sulfur-hetero-cyclic lower aryl group. Preferable group of these include a mono-cyclic, five or six membered cyclic, carbo- or one to five-oxygen, nitrogen, and/or sulfur hetero-cyclic, mono- or di-valent lower aroyl group optionally substituted by a lower alkyl, lower aryl, hydroxy, lower alkoxy, lower acyloxy, amino, lower alkylamino, lower acylamino, nitro group and/or halogen; lower alkoxycarbonyl optionally substituted by halogen; phenylsulfenyl optionally substituted by nitro or methoxy; or benzylidene optionally substituted by a lower alkyl, halogen, nitro, methoxy, and/or hydroxy. Typical example of these are benzoyl, 3-phenyl-5-methylisoxazole-4-carbonyl, isobutoxycarbonyl, 2,2,2-trichloroethoxycarbonyl, o-nitrophenylsulfenyl, benzylideneamino, or salicylideneamino group; or benzene-o-dicarbonyl group.

An important groups B include a group forming a lower alkyl ester, halo-lower alkyl ester, lower acyl-lower alkyl ester, lower alkoxy-lower alkyl ester, lower acyloxy-lower alkyl ester, lower aryl ester, lower aralkyl ester, carboxylic acid or its salt with an alkali metal, alkaline earth metal, lower alkylamine, lower arylamine, aromatic base, lower alkyltin, or lower alkylsilicon. These are, where possible, optionally substituted by a nitrogen, oxygen, sulfur, or carbon function and/or halogen. Preferable groups of them include methyl ester, 2,2,2-trichloroethyl ester, phenacyl ester optionally substituted by a halogen, methoxymethyl ester, lower alkanoyloxymethyl ester, benzyl ester optionally substituted by nitro, lower alkyl or halogen, or benzhydryl ester, free carboxylic acid or its salts with sodium, potassium, trimethylsilyl, trimethyltin, or triethylamine.

The most preferable halogen for Hal is chlorine.

The first type of the compounds are those of the general formula wherein the group D is a

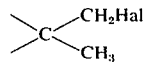

and *m* is zero; namely a 2'-halopenicillin compound of formula

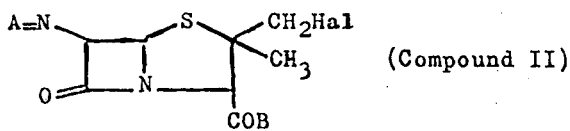

wherein A, B, and Hal are as defined above. The groups A and B are shown above in the item of the explanation of symbols. Important groups A are those consisting of a hydrogen and a lower carboxylic acyl group, carbonic acyl group, sulfonic acyl group; sulfenic acyl group, lower alkylidene group, or lower aralkylidene group; which can be substituted where possible by a nitrogen, oxygen, sulfur, or carbon function and/or halogen. Important groups B are that described above.

Specific examples of the 2'-halopenicillin compounds (II) include
methyl 2β-chloromethyl-2α-methyl-6β-phenoxyacetamidopenam-3α-carboxylate,
2,2,2-trichloroethyl 2β-chloromethyl-2α-methyl-6β-phenoxyacetamidopenam-3α-carboxylate,
p-nitrobenzyl 2β-chloromethyl-2α-methyl-6β-phenoxyacetamidopenam-3α-carboxylate,
p-bromophenacyl 2β-chloromethyl-2α-methyl-6β-phenoxyacetamidopenam-3α-carboxylate,
benzhydryl 2β-chloromethyl-2α-methyl-6β-phenoxyacetamidopenam-3α-carboxylate, pivaloyloxymethyl 2β-chloromethyl-2α-methyl-6β-phenoxyacetamidopenam 3α-carboxylate,
trimethylsilyl 2β-chloromethyl-2α-methyl-6β-phenoxyacetamidopenam-3α-carboxylate, 2β-chloromethyl-2α-methyl-6β-phenoxyacetamidopenam-3α-carboxylic acid,
benzhydryl 2β-bromomethyl-2α-methyl-6β-phenoxyacetamidopenam-3α-carboxylate,
2,2,2-trichloroethyl 2β-chloromethyl-2α-methyl-6β-phenylacetamidopenam-3α-carboxylate,
benzyl 2β-chloromethyl-2α-methyl-6β-phenylacetamidopenam-3α-carboxylate,
p-nitrobenzyl 2β-chloromethyl-2α-methyl-6β-phenylacetamidopenam-3α-carboxylate,
benzhydryl 2β-chloromethyl-2α-methyl-6β-phenylacetamidopenam-3α-carboxylate,
benzalamino 2β-chloromethyl-2α-methyl-6β-phenylacetamidopenam 3α-carboxylate,
2β-chloromethyl-2α-methyl-6β-phenylacetamidopenam-3α-carboxylic acid,
benzhydryl 2β-chloromethyl-2α-methyl-6β-(α-tert-butoxycarbonylaminophenylacetamido)penam-3α-carboxylate,
2β-chloromethyl-2α-methyl-6β-(α-tert-butoxycarbonylaminophenylacetamido)-penam-3α-carboxylic acid,
methyl 2β-chloromethyl-2α-methyl-6β-(α-acetamidophenylacetamido)penam-3α-carboxylate,
benzhydryl 2β-chloromethyl-2α-methyl-6β-norbornylcarbonylaminopenam-3α-carboxylate,
benzhydryl 2β-chloromethyl-2α-methyl-6β-ketopinoylaminopenam-3α-carboxylate,
benzhydryl 2β-chloromethyl-2α-methyl-6β-benzoylaminopenam-3α-carboxylate,
benzhydryl 2β-chloromethyl-2α-methyl-6β-(3-phenyl-5-methylisoxazol-4-carboxamido)penam-3α-carboxylate,
methyl 2(α and β)-chloromethyl-2(β and α)-methyl-6β-phthalimidopenam-3α-carboxylate,
2,2,2-trichloroethyl 2(α and β)-chloromethyl-2(β and α)-methyl-6β-phthalimidopenam-3α-carboxylate,
phenacyl 2(α and β)-chloromethyl-2(β and α)-methyl-6β-phthalimidopenam-3α-carboxylate,
benzhydryl 2(α and β)-chloromethyl-2(β and α)-methyl-6β-phthalimidopenam-3α-carboxylate,
benzyl 2(α and β)-chloromethyl-2(β and α)-methyl-6β-phthalimidopenam-3α-carboxylate,
benzhydryl 2β-chloromethyl-2α-methyl-6β-isobutoxycarbonylaminopenam-3α-carboxylate,
benzhydryl 2β-chloromethyl-2α-methyl-6β-(2,2,2-trichloroethoxycarbonylamino)penam-3α-carboxylate,
methoxymethyl 2ξ-chloromethyl-2ξ-methyl-6β-salicylideneaminopenam-3α-carboxylate,
benzhydryl 2ξ-chloromethyl-2ξ-methyl-6β-salicylideneaminopenam-3α-carboxylate,
benzhydryl 2ξ-chloromethyl-2ξ-methyl-6β-tritylaminopenam-3α-carboxylate,
anisyl 2ξ-chloromethyl-2ξ-methyl-6β-(2,2-dimethyl-4-phenyl-5-oxoimidazolidin-1-yl)penam-3α-carboxylate,
benzhydryl 2ξ-chloromethyl-2ξ-methyl-6β-(2,2-dimethyl-3-nitroso-5-oxo-4-phenylimidazolidin-1-yl)penam-3α-carboxylate,
benzhydryl 2β-chloromethyl-2α-methyl-6β-aminopenam-3α-carboxylate, and benzhydryl 2β-chloromethyl-2α-methyl-6β-thienylacetamidopenam-3α-carboxylate, The second type of the compounds are those of the general formula wherein the group D is a

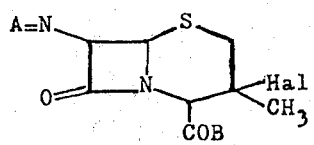

and m is zero, namely a 3-halo-3-methylcepham compound of formula

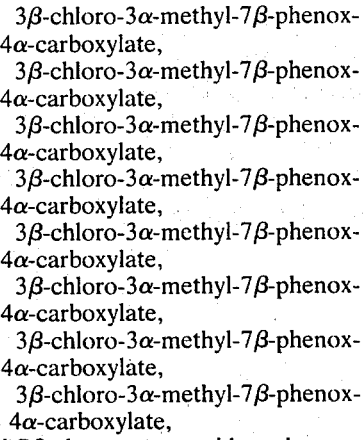

(Compound III)

wherein A, B and Hal are as defined above. The groups A, B and Hal are shown above in the item of the explanation of symbols. Important groups A are those consisting of a hydrogen and a lower aliphatic carboxylic acyl group, a mono- or bi-cyclic, five or six-membered cyclic, carbo- or one to five-nitrogen, oxygen and/or sulfur-hetero-cyclic lower aromatic carboxylic acyl group, carbonic acyl group, sulfonic acyl group, sulfenic acyl group, lower alkylidene group, or lower aralkylidene group, which are optionally substituted, where possible, by a nitrogen, oxygen, sulfur, or carbon function, and/or halogen. Important groups B are those described above, in which benzhydryl and phenacyl groups optionally substituted are most preferable.

Specific examples of the 3-halo-3-methylcepham compounds (III) include
methyl 3β-chloro-3α-methyl-7β-phenoxyacetamidocepham-4α-carboxylate,
2,2,2-trichloroethyl 3β-chloro-3α-methyl-7β-phenoxyacetamidocepham-4α-carboxylate,
benzyl 3β-chloro-3α-methyl-7β-phenoxyacetamidocepham-4α-carboxylate,
p-nitrobenzyl 3β-chloro-3α-methyl-7β-phenoxyacetamidocepham-4α-carboxylate,
p-bromophenacyl 3β-chloro-3α-methyl-7β-phenoxyacetamidocepham-4α-carboxylate,
pivaloyloxymethyl 3β-chloro-3α-methyl-7β-phenoxyacetamidocepham-4α-carboxylate,
benzhydryl 3β-chloro-3α-methyl-7β-phenoxyacetamidocepham-4α-carboxylate,
trimethylsilyl 3β-chloro-3α-methyl-7β-phenoxyacetamidocepham- 4α-carboxylate,
3β-chloro-3α-methyl-7β-phenoxyacetamidocepham-4α-carboxylic acid, benzhydryl 3β-fluoro-3α-methyl-7β-phenoxyacetamidocepham-4α-carboxylate,
methyl 3β-chloro-3α-methyl-7β-phenylacetamidocepham-4α-carboxylate,
2,2,2-trichloroethyl 3β-chloro-3α-methyl-7β-phenylacetamidocepham-4α-carboxylate,
p-nitrobenzyl 3β-chloro-3α-methyl-7β-phenylacetamidocepham-4α-carboxylate,
benzhydryl 3β-chloro-3α-methyl-7β-phenylacetamidocepham-4α-carboxylate,
benzalamino 3β-chloro-3α-methyl-7β-phenylacetamidocepham-4α-carboxylate,
benzhydryl 3β-chloro-3α-methyl-7β-(α-tert-butoxycarbonylaminophenylacetamido)cepham-4α-carboxylate,
3β-chloro-3α-methyl-7β-phenylglycylaminocepham-4α-carboxylic acid, benzhydryl 3β-chloro-3α-methyl-7β-norbornylcarboxamidocepham-4α-carboxylate, benzhydryl 3β-chloro-3α-methyl-7β-ketopinoylaminocepham-4α-carboxylate,
3β-chloro-3α-methyl-7β-ketopinoylaminocepham-4α-carboxylic acid, methyl 3β-chloro-3α-methyl-7β-phthalimidocepham-4α-carboxylate, benzhydryl 3β-chloro-3α-methyl-7β-(3-phenyl-5-methylisoxazol-4-carboxamido)cepham-4α-carboxylate,
3β-chloro-3α-methyl-7β-(3-phenyl-5-methylsoxazol-4-carboxamido)-cepham-4α-carboxylic acid,
benzhydryl 3β-chloro-3α-methyl-7β-isobutoxycarbonylaminocepham-4α-carboxylate,
benzhydryl 3β-chloro-3α-methyl-7β-(2,2-dimethyl-4-phenyl-5-oxoimidazolidin-1-yl)cepham-4α-carboxylate, and
benzhydryl 3β-chloro-3α-methyl-7β-tritylaminocepham-4α-carboxylate.

The third type of the compounds are those of the general formula wherein the group D is a

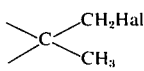

group, and m is one, namely a 2'-halopenicillin-1-oxide compound of the formula

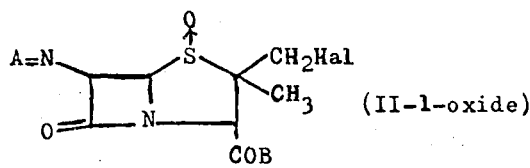

wherein A, B, and Hal are as defined above. The groups A, B, and Hal are shown above in the item of the explanation of symbols. Preferable groups A include that consisting of a hydrogen and an acyl group of the formula

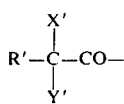

wherein R' is a hydrogen or a lower alkyl group, a lower cycloalkyl group, a lower aralkyl group, or mono- or bi-cyclic, five or six-membered cyclic, a carbo- or one to five-nitrogen, oxygen, and/or sulfur-hetero-cyclic lower aryl group, which are, where possible, optionally unsaturated or substituted by an oxygen, sulfur, nitrogen, and/or carbon function, or a halogen; X' is a hydrogen or an oxygen, sulfur, nitrogen, or carbon function or halogen, or R', C and X' combined together represents a lower alicyclic group; and Y is a hydrogen or a group cited for R' and X'. More preferable group of them include a group of formula

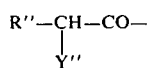

wherein R'' is a hydrogen, a lower alkyl group, a cyano group, or a mono-cyclic, carbo- or one to five-nitrogen, oxygen, and/or sulfur-heterocyclic lower aryl group; and Y'' is a hydrogen or a lower alkanoyloxy; lower aryloxy, hydroxy, amino optionally substituted by a lower alkoxycarbonyl, lower alkylthio, amidinothio, lower arylthio, lower aralkylthio, lower alkyl, or combined together with R'' and C forms a lower alicyclic group; all optionally unsaturated or substituted by a nitrogen, oxygen, sulfur, and/or carbon function, or halogen. Typical example of these are phenoxyacetyl, phenylacetyl, thienylacetyl, phenylglycyl optionally substituted by a lower alkoxycarbonyl group, 2-ketopinoyl, or norbornanecarbonyl group. Other type of preferable amino-substituents include that consisting of a hydrogen and a mono- or bi-cyclic, 5 or 6-membered cyclic, carbo- or one to five-nitrogen, oxygen, and/or sulfur-hetero-cyclic aromatic monovalent lower carboxylic acyl; carbonic acyl; sulfonic acyl; sulfenic acyl; lower alkyl; lower alkylidene; or lower aralkylidene. They can optionally be unsaturated or substituted, where possible, by a halogen or a lower alkyl, lower aryl, lower aralkyl, hydroxy, lower alkoxy, lower acyloxy, amino, lower alkylamino, lower acylamino, nitro, and/or lower alkylthio group; and that combined with the nitrogen of A=N group to form imide, i.e. a di-valent lower carboxylic acyl group of lower aliphatic or mono-cyclic, carbo- or one to five-nitrogen, oxygen, and/or sulfur-hetero-cyclic lower aryl group. More preferable group of these include a mono-cyclic, five or six membered-cyclic, carbo- or one to five-oxygen, nitrogen, and/or sulfur heterocyclic, mono- or di-valent lower aroyl group optionally substituted by a lower alkyl, lower aryl, hydroxy, lower alkoxy, lower acyloxy, amino, lower alkylamino, lower acylamino, nitro, and/or halogen; lower alkoxycarbonyl optionally substituted by halogen; phenylsulfenyl optionally substituted by nitro or methoxy; or benzylidene optionally substituted by a lower alkyl, halogen, nitro, methoxy, and/or hydroxy. Typical example of these are benzoyl, 3-phenyl-5-methylisoxazole-4-carbonyl, isobutoxycarbonyl, 2,2,2-trichloroethoxycarbonyl, o-nitrophenylsulfenyl, benzylideneamino, or salicylideneamino group; or benzene-o-dicarbonyl group.

A preferable groups B include a group forming a lower alkyl ester, halo-lower alkyl ester, lower acyl-lower alkyl ester, lower alkoxy-lower alkyl ester, lower acyloxy-lower alkyl ester, lower aryl ester, lower aralkyl ester, carboxylic acid, or its salt with an alkali metal, alkaline earth metal lower alkylamine, lower arylamine, lower aromatic base, lower alkyl-tin, or lower alkyl-silicon, all where possible, optionally unsaturated or substituted by nitrogen, oxygen, sulfur, or carbon function and/or halogen. More preferably groups of them include methyl ester, 2,2,2-trichloroethyl ester, phenacyl ester optionally substituted by a halogen, methoxymethyl ester, lower alkanoyloxymethyl ester, benzyl ester optionally substituted by nitro, lower alkyl or halogen, or benzhydryl ester, free carboxylic acid or its salts with sodium, potassium, trimethylsilyl, trimethyltin, or triethylamine. The most preferable halogen for Hal is chlorine.

Specific examples of the 2'-halopenicillin-1-oxide compounds (II-1-oxide) include
methyl 2β-chloromethyl-2α-methyl-6β-phenoxyacetamidopenam-3α-carboxylate 1(α and β)-oxide,
2,2,2-trichloroethyl 2β-chloromethyl-2α-methyl-6β-phenoxyacetamidopenam-3α-carboxylate 1β-oxide,
benzyl 2β-chloromethyl-2α-methyl-6β-phenoxyacetamidopenam-3α-carboxylate 1β-oxide,
benzhydryl 2β-chloromethyl-2α-methyl-6β-phenoxyacetamidopenam-3α-carboxylate 1β-oxide, benzhydryl 2β-chloromethyl-2α-methyl-6β-phenoxyacetamidopenam-3α-carboxylate 1α-oxide,
benzyl 2β-chloromethyl-2α-methyl-6β-phenylacetamidopenam-3α-carboxylate 1β-oxide,
benzhydryl 2β-chloromethyl-2α-methyl-6β-phenylacetamidopenam-3α-carboxylate 1β-oxide,
benzhydryl 2β-chloromethyl-2α-methyl-6β-(α-tert-butoxycarbonylaminophenylacetamido)penam-3α-carboxylate 1β-oxide,
methyl 2α-chloromethyl-2β-methyl-6β-phthalimidopenam-3α-carboxylate 1α-oxide,
methyl 2β-chloromethyl-2α-methyl-6β-phthalimidopenam-3α-carboxylate 1α-oxide,
phenacyl 2α-chloromethyl-2β-methyl-6β-phthalimidopenam-3α-carboxylate 1α-oxide,
phenacyl 2β-chloromethyl-2α-methyl-6β-phthalimidopenam-3α-carboxylate 1β-oxide,
2α-chloromethyl-2β-methyl-6β-phthalimidopenam-3α-carboxylic acid 1α-oxide,
methyl 2α-bromomethyl-2β-methyl-6β-phthalimidopenam-3α-carboxylate 1α-oxide,
methyl 2α-fluoromethyl-2β-methyl-6β-phthalimidopenam-3α-carboxylate 1α-oxide,
methoxymethyl 2β-chloromethyl-2α-methyl-6β-(5-methyl-3-phenylisoxazole-carboxamido)penam-3α-carboxylate 1β-oxide,
methoxymethyl 2ξ-chloromethyl-2ξ-methyl-6β-salicylideneaminopenam-3α-carboxylate 1ξ-oxide,
benzhydryl 2β-chloromethyl-2α-methyl-6β-(2,2,2-trichloroethoxycarbonylamino)penam-3α-carboxylate 1β-oxide,
benzhydryl 2β-chloromethyl-2α-methyl-6β-(2,2,2-trichloroethoxycarbonylamino)penam-3α-carboxylate 1α-oxide,
benzhydryl 6β-amino-2β-chloromethyl-2α-methylpenam-3α-carboxylate 1(α and β)-oxide, and
benzhydryl 2β-chloromethyl-2α-methyl-6β-(o-nitrophenylsulfenylamino)-penam-3α-carboxylate 1-oxide.

The fourth type of the compounds are those of the general formula wherein the group D is a

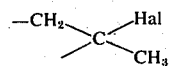

group, and m is one, namely a 3-halo-3-methylcepham-1-oxide compound of formula

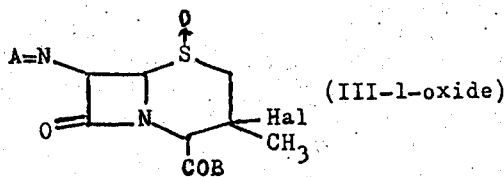

(III-1-oxide)

wherein A, B, and Hal are as defined above. The groups A, B, and Hal are shown above in the item of explanation of the symbols. Preferred groups A include that consisting of a hydrogen and an acyl group of the formula

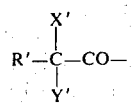

wherein R' is a hydrogen or a lower alkyl group, a lower cycloalkyl group, a lower aralkyl group, or mono- or bi-cyclic, five or six-membered cyclic, a carbo- or one to five-nitrogen, oxygen and/or sulfur-hetero-cyclic lower aryl group, which are, where possible, optionally unsaturated or substituted by an oxygen, sulfur, nitrogen, and/or carbon function, or a halogen; X' is a hydrogen or an oxygen, sulfur, nitrogen, or carbon function or halogen, or R', C and X' combined together represents a lower alicyclic group; and Y is a hydrogen or a group cited for R' and X'. More preferable group of them include a group of formula

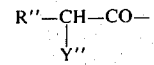

wherein R'' is a hydrogen, a lower alkyl group, a cyano group, or a mono-cyclic, carbo- or one to five-nitrogen, oxygen, and/or sulfur-heterocyclic lower aryl group, and Y'' is a hydrogen or a lower alkanoyloxy; lower aryloxy; hydroxy; amino optionally substituted by a lower alkoxycarbonyl; lower alkylthio; amidinothio; lower arylthio; lower aralkylthio; lower alkyl; or combined together with R'' and C forms a lower alicyclic group; all optionally unsatd. or substituted by a nitrogen, oxygen, sulfur, and/or carbon function, or halogen. Typical example of these are phenoxyacetyl, phenylacetyl, thienylacetyl, phenylglycyl optionally substituted by a lower alkoxycarbonyl group, 2-ketopinoyl, or norbornanecarbonyl group. Other type of preferable amino-substituents include that consisting of a hydrogen and a mono- or bi-cyclic, five or six-membered cyclic, carbo- or one to five nitrogen, oxygen, and/or sulfur-heterocyclic aromatic mono-valent carboxylic acyl; carbonic acyl; sulfonic acyl; sulfenic acyl; lower alkyl; lower alkylidene, or lower aralkylidene, all of these are optionally unsaturated or substituted where possible, by a halogen or a lower alkyl, lower aryl, lower aralkyl, hydroxy, lower alkoxy, lower acyloxy, amino, lower alkylamino, lower acylamino, nitro, and/or alkylthio group; and that combined with the nitrogen of A=N group to form imide, i.e. a bivalent lower carboxylic acyl group of lower aliphatic or mono-cyclic, carbo- or one to five-nitrogen, oxygen, and/or sulfur-hetero-cyclic lower aryl group. More preferable group of these include a mono-cyclic, five or six membered-cyclic, carbo- or one to five-oxygen, nitrogen, and/or sulfur heterocyclic, mono- or bi-valent lower aroyl group optionally substituted by a lower alkyl, lower aryl, hydroxy, lower alkoxy, lower acyloxy, amino, lower alkylamino, lower acylamino, nitro, and/or halogen; lower alkoxycarbonyl optionally substituted by halogen; phenylsulfenyl optionally substituted by nitro or methoxy; or benzylidene optionally substituted by a lower alkyl, halogen, nitro, methoxy, and/or hydroxy. Typical example of these are benzoyl, 3-phenyl-5-methylisoxazole-4-carbonyl, isobutoxycarbonyl, 2,2,2-trichloroethoxycarbonyl, o-nitrophenylsulfenyl, benzylideneamino, or salicylideneamino group; or benzene-o-dicarbonyl group.

A preferable groups B include a group forming a lower alkyl ester, halo-lower alkyl ester, lower acyl-lower alkyl ester, lower alkoxy-lower alkyl ester, lower acyloxy-lower alkyl ester, lower aryl ester, lower aralkyl ester, carboxylic acid, or its salt with an alkali metal, alkaline earth metal, lower alkylamine, lower arylamine, lower aromatic base, lower alkyltin or lower alkylsilicon; all, where possible, optionally unsaturated or substituted by a nitrogen, oxygen, sulfur, or carbon function and/or halogen. More preferable groups of them include methyl ester, 2,2,2-trichloroethyl ester, phenacyl ester optionally substituted by a halogen, methoxymethyl ester, lower alkanoyloxymethyl ester, benzyl ester optionally substituted by nitro, lower alkyl or halogen, or benzhydryl ester, free carboxylic acid or its salts with potassium, trimethylsilyl, trimethyltin, sodium or triethylamine. The most preferable halogen for Hal is chlorine.

Specific examples of the 3-halo-3-methylcepham-1-oxide compounds (III-1-oxide) include
benzhydryl 3β-chloro-3α-methyl-7β-phenoxyacetamidocepham-4α-carboxylate 1β-oxide,
benzyl 3β-chloro-3α-methyl-7β-phenylacetamidocepham-4α-carboxylate 1β-oxide,
benzhydryl 3β-chloro-3α-methyl-7β-(α-tert-butoxycarbonylaminophenylacetamido)cepham-4α-carboxylate 1β-oxide,
methoxymethyl 3β-chloro-3α-methyl-7β-salicylideneaminocepham-4α-carboxylate 1ξ-oxide,
p-bromophenacyl 3β-chloro-3α-methyl-7β-(2,2,2-trichloroethoxycarbonylamino)cepham-4α-carboxylate 1β-oxide,
benzhydryl 3-chloro-3-methyl-7β-(5-methyl-3-phenylisoxazol-4-carboxamido)cepham-4α-carboxylate 1β-oxide,
methyl 3β-chloro-3α-methyl-7β-phthalimidocepham-4α-carboxylate 1ξ-oxide, and
3β-chloro-3α-methyl-7β-phenoxyacetamidocepham-4α-carboxylic acid 1β-oxide.

The antibacterial compounds II, III, and 1-oxides of those can be used as medicines for humans and warm blooded animals optionally in admixture with a conventional pharmaceutical carrier. They can be used for the prevention or treatment of bacterial infections caused by Gram positive and negative bacteria, at a dose of 0.1 to 10 g per kilogram body weight per day. They can also be used for the treatment of plant diseases caused by bacteria, or for the prevention of or stopping of decay of perishables. They are also useful as intermediates for the production of some other antibacterials, including cephalexin, by the methods described in the present specification and by conventional methods in the art. Among the compounds, those having a hydroxy group as B are more potent antibacterials. 1-Oxides are weaker antibacterials.

The pharmaceutical carrier for the compounds can be a solid or liquid in which the compounds are dissolved, dispersed, or suspended. Solid compositions can take the form of tablets, powders, vials, granules, capsules, pills or like forms. Liquid composition can take the form of injections, ointments, suspensions, solutions, emulsions, syrups, elixirs, or like forms. Preparations can be flavoured, coloured, or coated. The carrier may include diluents (e.g. starch, sucrose, lactose, calcium carbonate, kaolin); colouring agents; aromatic substances; bulking agents (e.g. lactose, salt, glycine, starch, calcium carbonate, kaolin, bentonite, calcium phosphate); binders (e.g. starch, acacia, gelatin, glucose, sodium alginate, tragacanth, carboxymethylcellulose); disintegrators (e.g. starch, agar, carbonates); lubricants (e.g. stearic acid, talc, paraffin, boric acid, sodium benzoate, Carbowax, cacao oil); ointment bases (e.g. fats, oils, lard, wool fat, vaselin, glycerin, resins, glycols); emusifying agents; solvents (e.g. water, polyethylene glycol, olive oil, sesame oil, cacao oi, methyl or ethyl oleate); solubilizing agents; buffers; and stabilizing agents. Vials for injection and capsules for oral administration can contain pure powder or crystals of the compounds, together with additives such as stabilizers or co-acting substances, if required.

REACTION I: PREPARATION OF 2'-HALOPENICILLIN COMPOUNDS

A 2'-halopenicillin compound of formula

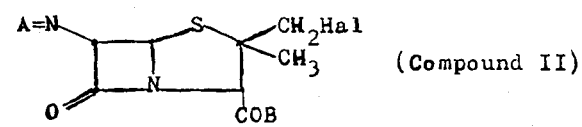

(Compound II)

wherein A is two hydrogens or amino-substitutent, B is a hydroxy or a carboxy-protecting group, and Hal is a halogen, is prepared by the reaction of a penicillin-1-oxide compound of formula

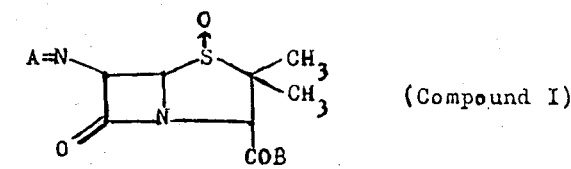

(Compound I)

wherein A and B are as defined above, with an acid halide in the presence of a base, the desired product being isolable in the crude or pure state.

The groups A and B are shown above in the item of the explanation of symbols. Preferable groups A include two hydrogens or an amino-substituent, in which the amino-substituent can be a hydrogen and a mono-valent amino-substituent, two mono-valent amino-substituents, or a di-valent amino-substituent. Representative amino-substituents are a lower hydrocarbon group, an inorganic acyl group, organic acyl group, and tri-lower alkylsilyl group. The representative mono-valent lower hydrocarbon groups include a lower alkyl, lower unsaturated hydrocarbon group, five or six-membered cyclic, mono- or bi-cyclic, carbo- or one to five nitrogen-, oxygen- and/or sulfur-hetero-cyclic, lower aromatic group, lower aralkyl, and like groups. Representative di-valent lower hydrocarbon groups include a lower alkylidene, lower aralkylidene, and like groups. These mono- or di-valent lower hydrocarbon groups can be unsaturated or substituted by a substituent linked through carbon, oxygen, sulfur, or nitrogen, and/or by halogen. The substituted groups are useful when the substitution renders the group easy to remove, or when the substitution make the compounds pharmaceutically favourable. Representative mono-valent inorganic acyl groups include a substituted carbonic acyl, substituted sulfuric acyl, substituted phosphoric acyl, and like groups. Representative di-valent inorganic acyl groups include a carbonyl, lower alkylaminomethoxymethylidene, and the like. Representative organic acyl groups are acyl groups derived from a lower carboxylic, sulfonic, sulfenic, or phosphonic or like acids. Some compounds having these groups show storng antibacterial activity. Representative monovalent organic acyl groups include a sulfonic acyl group, sulfenic acyl group, phosphonic acyl group, and carboxylic acyl group. Preferable organic acyl groups include those of formula

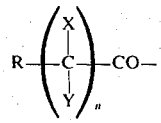

wherein $n$ is zero or one; and R is a hydrogen or a hydrocarbon group (e.g. a straight, branched, or cylic lower alkyl, lower aralkyl, or five or six-membered cyclic, mono- or di-cyclic, carbo- or one to five nitrogen-, oxygen-, and/or sulfur-hetero-cyclic lower aryl); X is a hydrogen or an oxygen, sulfur, nitrogen, or carbon function, or halogen; Y is a hydrogen or one of the groups cited for the groups R and X. Y and R and/or X can be combined to form a cyclic group. All of these groups can be, where possible, unsaturated or substituted by an oxygen, sulfur, nitrogen, or carbon function, or by halogen. Specific examples of these are a lower alkanoyl, unsaturated lower aliphatic carboxylic acyl, lower aliphatic carboxylic acyl substituted by an oxygen, sulfur, nitrogen, or carbon function, or halogen; lower aralkylcarboxylic acyl optionally substituted by an oxygen, nitrogen, sulfur, or carbon function, or by halogen, and mono- or bi-cyclic, five or six-membered cyclic, carbo- or one to five-nitrogen, oxygen, or sulfur-hetero-cyclic, aromatic lower carboxylic acyl. These acyl groups can, where possible, be unsaturated or substituted by an oxygen, sulfur, nitrogen, or carbon function, halogen, or other substituents as cited above. Representative di-valent organic acyl groups include aliphatic or aromatic di-valent acyl groups, forming an imide group when combined with the nitrogen in the group A=N. Other type of the amino-substituents include those consisting of a mono-valent acyl group and a mono-valent lower hydrocarbon group both can be combined, or of two mono-valent acyl groups. Among these, preferable acyl groups are those of the formula

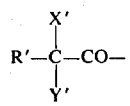

wherein R' is a hydrogen or a lower alkyl group, a lower cycloalkyl group, a lower aralkyl group, or mono- or bi-cyclic, five or six-membered cyclic, a carbo- or one to five-nitrogen, oxygen, and/or sulfur-hetero-cyclic lower aryl group, which are, where possible, optionally unsaturated or substituted by an oxygen, sulfur, nitrogen, and/or carbon function, or a halogen; X' is a hydrogen or an oxygen, sulfur, nitrogen, or carbon function, or halogen, or R', C, and X' combined together represents a lower alicyclic group; and Y is a hydrogen or a group cited for R' and X'. More preferable group of them include a group of formula

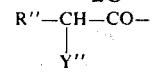

wherein R'' is a hydrogen, a lower alkyl group, a cyano group, or a mono-cyclic, carbo- or one to five-nitrogen, oxygen, and/or sulfur-heterocyclic lower aryl group, and Y'' is a hydrogen or a lower alkanoyloxy, lower aryloxy, hydroxy, amino optionally substituted by a lower alkoxycarbonyl, lower alkylthio, amidinothio, lower arylthio, lower aralkylthio, lower alkyl, or combined together with R'' and C forms a lower alicyclic group; all optionally substituted by a nitrogen, oxygen, sulfur, and/or carbon function, or halogen. Typical example of these are phenoxyacetyl phenylacetyl, thienylacetyl, phenylglycyl, optionally substituted by a lower alkoxycarbonyl, 2-ketopinoyl, or norbornanecarbonyl. Other type of preferable amino-substituents include that consisting of a hydrogen and a mono- or bi-cyclic, five or six membered cyclic, carbo- or one to five-nitrogen, oxygen, and/or sulfur-heterocyclic aromatic mono-valent carboxylic acyl; carbonic acyl; sulfonic acyl; sulfenic acyl, lower alkyl, lower alkylidene, or lower aralkylidene, all of these are optionally unsaturated or substituted, where possible, by a halogen or a lower alkyl, lower aryl, lower aralkyl, hydroxy, lower alkoxy, lower acyloxy, amino, lower alkylamino, lower acylamino, nitro, and/or lower alkylthio group; and that combined with the nitrogen or A=N group to form imide, i.e. a di-valent lower carboxylic acyl group of lower aliphatic or mono-cyclic, carbo- or one to five-nitrogen, oxygen, and/or sulfur-hetero- cyclic lower aryl group. More preferable group of these include a mono-cyclic, five or six-membered cyclic, carbo- or one to five-oxygen, nitrogen, and/or sulfur heterocyclic, mono- or bi-valent lower aroyl group optionally substituted by a lower alkyl, lower aryl, hydroxy, lower alkoxy, lower acyloxy, amino, lower alkylamino, lower acylamino, nitro, and/or halogen; lower alkoxycarbonyl optionally substituted by halogen; phenylsulfenyl optionally substituted by nitro or methoxy; or benzylidene optionally substituted by a lower alkyl, halogen, nitro, methoxy, and/or hydroxy. Typical example of these are benzoyl, 3-phenyl-5-methylisoxazole-4-carbonyl, isobutoxycarbonyl, 2,2,2-trichloroethoxycarbonyl, o-nitrophenylsulfenyl, benzylideneamino, or salicylideneamino group; or benzene-o-dicarbonyl group. Representative groups B include hydroxyl and a carboxy-protecting group. The carboxy-protecting group, taken together with the adjacent CO group, include an ester, anhydride, or salt when B is an oxygen function; and amide, imide, or azide when B is a nitrogen function; and a thiol ester of thiol acid when B is a sulfur function. Preferable esters includes ester with a lower aliphatic alcohol, lower aromatic hydroxy compound, lower aralkyl alcohol, hydroxylamines, and the like; Representative salts include alkali metal salts, alkaline earth metal salts, silyl esters, tin esters, organic base salts, and the like. Representative amides include unsubstituted amides and substituted amides. The ester, amide and imide groups stated above can be substituted by oxygen, nitrogen, sulfur, or carbon function, or by halogen, or unsaturated, where possible. Preferable of these include a halo-lower alkyl ester, lower acyl-lower alkyl ester, lower alkoxy-lower alkyl ester, lower acyloxy-lower alkyl ester, 1,1-dicarbo-lower alkyloxy-alkyl ester, lower aryl ester, lower aralkyl ester, ester with hydroxylamines, amide, and carboxylic acid or its salt with alkali metal, alkaline earth metal, lower alkylamine, lower arylamine, lower aromatic base, lower alkyl-tin, or lower alkylsilicon, all of these, where possible, optionally unsaturated or substituted by a nitrogen, oxygen, sulfur, or carbon function, and/or halogen. More preferable groups of them include methyl ester, 2,2,2-trichloroethyl ester, phenacyl ester optionally substituted by a halogen, methoxymethyl ester, lower alkanoyloxymethyl ester, benzyl ester optionally substituted by nitro, lower alkyl or halogen, or benzhydryl ester, free carboxylic acid or its salts with sodium, potassium, trimethylsilyl, trimethyltin, or triethylamine. The most preferable halogen for Hal is chlorine.

The acid halide for this purpose may be a lower aliphatic carboxylic acid halide (e.g. acetyl chloride, chloroacetyl chloride, propionyl bromide, oxalyl chloride, adamantoyl chloride, crotonyl chloride, ethylnylacetylchloride), lower aralkyl carboxylic acid halide (e.g. phenylacetyl chloride, thiopheneacetyl chloride), a mono-, bi- or tri-cyclic, carbo- or hetero-cyclic lower aromatic carboxylic acid halide (e.g. benzoyl chloride, benzoyl bromide, benzoyl iodide, benzoyl fluoride, benzoyl chlorides substituted by nitro, methoxy, lower alkyl, halogen, and the like, naphthoyl chloride, thienoyl chloride, nicotinoyl chloride, quinolinecarbonyl chloride), lower aliphatic sulfonic acid halide (e.g. methanesulfonyl chloride, ethanesulfonyl chloride, cyclohexylsulfonyl chloride, cyclopentylacetyl chloride), mono-, bi- or tri-cyclic, carbo- or one to five-nitrogen, oxygen, and/or sulfur hetero-cyclic lower aromatic sulfonic acid halide (e.g. benzenesulfonyl chloride optionally substituted by lower alkyl, methoxy, nitro, or halogen, toluene-p-sulfonyl bromide, naphthalenesulfonyl chloride, quinoline-8-sulfonyl chloride, 1,3,4-thiadiazolylsulfonyl chloride); lower aliphatic or monocyclic aromatic hydrocarbyl haloformate (e.g. methyl chloroformate, phenyl chloroformate, methyl bromoformate); or other acid halides capable of contributing to this reaction. Preferable acid halides include acetyl chloride, propionyl chloride, pivaloyl chloride, oxalyl chloride, benzoyl fluoride, benzoyl chloride and bromide, p-nitrobenzoyl chloride, p-anisoyl chloride, toluene-p-sulfonyl chloride, methanesulfonyl chloride, and ethyl chloroformate.

The base for this purpose may be an inorganic base (e.g. alkali metal or alkaline earth metal carbonates such as sodium hydrogen carbonate, potassium hydrogen carbonate, sodium carbonate, potassium carbonate, calcium carbonate), an organic base (e.g. a lower aliphatic hydrocarbyl amine such as dimethylamine, trimethylamine, triethylamine, N-methylpiperidine, N-methylmorpholine, N-ethylpyrrolidine, or N,N-dimethylbenzylamine; or a mono-, bi- or tri-cyclic, homo- or hetero-cyclic aromatic amine such as pyridine, picoline, lutidine, quinoline, isoquinoline, or N,N-dimethylanilin), or other base (e.g. urea, thiourea, guanidine, N-lower alkylurea compounds, N-lower alkylthiourea, Schiff bases). Preferable bases include pyridine, picoline, lutidine, triethylamine, and trimethylamine.

The reaction is preferably carried out in an inert solvent, at a temperature of higher than 40°C, with not less than about 1 mole equivalent of the acid halide for 1 mole equivalent of the penicillin-1-oxide compound. Preferable temperature is in the range of 70°C to 130°C, and particularly from 80°C to 120°C. The molar ratio of the acid halide is usually between about 1 and 10 mole equivalents, preferably 1 to 2 mole equivalents, to 1 mole equivalent of the penicillin-1-oxide compound. In preferable conditions, the reaction is complete within 0.5 to 20 hours, the duration depending on the nature of the starting material, reagents, and reaction conditions. The representative inert solvent is a hydrocarbon (e.g. pentane, hexane, petroleum ether, isooctane, decaline, benzene, toluene, xylene, mesitylene, naphthalene), halohydrocarbon (e.g. methylene chloride, chloroform, tetrachloroethane, chlorobenzene, dichlorobenzene, bromobenzene), ether (e.g. diethyl ether, tetrahydrofuran, tetrahydropyran, diglyme, diethyleneglycol dimethyl ether, dioxane), ketone (e.g. acetone, methyl ethyl ketone, methyl isobutyl ketone, cyclohexanone, acetophenone, benzophenone), ester (e.g. ethyl acetate, butyl acetate, isobutyl acetate, amyl acetate, ethyl propionate, ethyl benzoate, amyl benzoate), amide (e.g. formamide, N,N-dimethylformamide, N,N-dimethylacetamide, hexamethylphosphoramide, N-acetylmorpholine), nitrohydrocarbon (e.g. nitromethane, nitrobenzene), nitrile (e.g. acetonitrile, benzonitrile), or a mixture of these inert solvents. Preferable solvents or solvent mixture are those boiling in the range of 70°C to 150°C. Lower boiling solvents can be used under pressure. Preferable solvents are benzene, toluene, dioxane, tetrahydrofuran, N,N-dimethylformamide, N,N-dimethylacetamide and hexamethylphosphoramide. The reaction solution can be stirred, and protected from air or moisture with an inert gas e.g. nitrogen, or argon. When the base is omitted, no reaction takes place, and the unreacted acid halide and penicillin-1-oxide compound recovered. The reaction can be carried out with an equimolar adduct of a base and an acid halide, i.e. the reagents can be mixed previously to form an onium salt adduct (e.g. in the case of pyridine and benzoyl chloride to form N-benzoyl-pyridinium chloride) which can be used in place of the component reagents. Both 1α- and 1β-oxides give the same β-halopenicillin in which the halomethyl group is in β configuration when A=N is an amido group; and they give a mixture of α-and β-halomethyl compounds when the 6-substituent has no hydrogen on the nitrogen atom of A=N is imido group.

The compounds II are novel compounds; they can be purified and isolated according to conventional methods. They show antibacterial activity and can be used as medicines or disinfectants in conventional formulations with conventional carriers. For human or warm-blooded animal use, the daily dose is unsually in the range of 0.1 mg to 10 g per kilogram body weight. They can also be used as intermediates for the preparation of other antibacterial compounds.

REACTION II: PREPARATION OF 3-HALO-3-METHYLCEPHAM COMPOUNDS

Heating a 2'-halopenicillin compound of formula

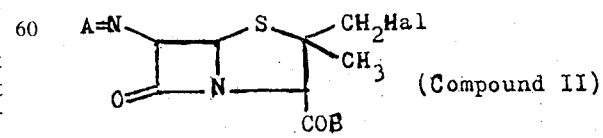

(Compound II)

wherein A, B, and Hal are as defined above, gives a 3-halo-3-methylcepham compound of formula

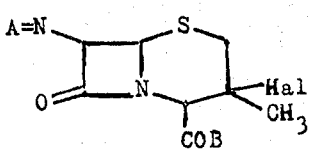

(Compound III)

wherein A, B, and Hal are as defined above.

The preferable groups for A and B are described in the explanation of the symbols. Preferable groups for A and B are also shown in the item of Reaction I. Important groups for A in this reaction II are those consisting of a hydrogen and a lower carboxylic acyl group, carbonic acyl group, sulfonic acyl group; sulfenic acyl group, lower alkylidene group, or lower aralkylidene group; which can be substituted, where possible, by a nitrogen, oxygen, sulfur, or carbon function, and/or halogen. Important groups B are that described in the item of explanation of symbols, and of Reaction I.

The temperature for heating is usually from 70°C to 200°C, especially in the range from 90°C to 130°C when Hal is chlorine. The higher the reaction temperature, more is cephem compound IV of the following formula formed as a by-product.

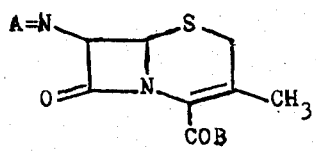

(Compound IV)

wherein A and B are as defined above.

The reaction can preferably be carried out in one of the hydrocarbon, halohydrocarbon, ether, ketone, ester, amide, nitrohydrocarbon, or nitrile solvents given in the Reaction I section; or in another solvent such as a sulfoxide, (e.g. dimethyl sulfoxide, diethyl sulfoxide, thian-1-oxide), alcohol (e.g. methanol, ethanol, propanol, tert-butanol, octanol, phenol), organic acid (e.g. formic acid, acetic acid, propionic acid, valeric acid), water, or in a mixture of these solvents. Lower boiling solvents can be used under pressure. Preferable solvents are dimethyl sulfoxide, N,N-dimethylformamide, N,N-dimethylacetamide, hexamethylphosphoramide, dioxane, acetic acid, and water, of their mixtures. Preferable solvents or solvent mixtures have usually dielectric constants of not less than 10, and especially in the range of from 30 to 100. With pure pyridine as solvent, the yield is very low. The reaction may be carried out under an inert gas such as nitrogen, carbon dioxide, or argon. The reaction solution may be stirred.

No example is known in the literature relating to the conversion of a 2-acetoxymethyl-2-methylpenam compound to give a 3-cephem compound or a 3-acetoxycepham compound.

The compounds III are new antibacterial compounds and are useful medicinally as antibacterials or disinfectants in doses ranging from 0.1 to 10 g per kilogram body weight per a day for humans or warm-blooded animals when administered orally or by injection. The compounds are also useful as starting materials for the synthesis of other useful compounds e.g. cephalexin, by way of the Reaction III, and other methods.

REACTION III: 3-METHYLCEPHEM COMPOUNDS FROM 3-HALO-3-METHYLCEPHAM COMPOUNDS

A 3-halo-3-methylcepham compound of formula

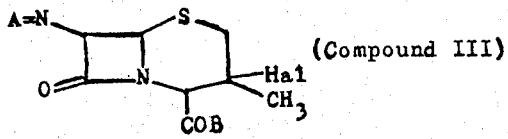

(Compound III)

wherein A, B, and Hal are as defined above, when heated in the presence or absence of a pseudo-base gives a 3-methyl-3-cephem compound of formula

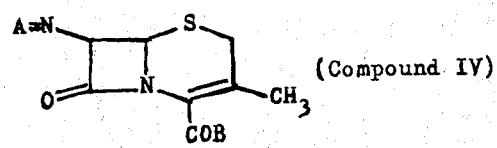

(Compound IV)

wherein A and B are as defined above.

The reaction proceeds satisfactorily in the absence of the pseudo-base. The reaction is effected by heating compound III, preferably in a solvent, at a temperature of from 50°C to 200°C, especially from 70°C to 150°C and preferably from 90°C to 130°C. The solvent can be one of those cited in the Reaction II section. Preferable solvents include dimethyl sulfoxide, N,N-dimethylformamide, N,N-dimethylacetamide, and dioxane. The reaction is usually complete within 0.5 to 5 hours at 80°C to 130°C. No detective amount of the corresponding 2-cephem compounds has been found in the reaction mixture, which is easily worked up. In the absence of an inorganic or organic base, the reaction takes place more cleanly and the reaction mixture is easy to handle. The pseudo base for this reaction is a weak base e.g. urea, thiourea, and guanidine. These pseudo bases affect on the reaction to less extent but may keep the reaction mixture neutral.

The products of this reaction are 3-methyl-3-cephem compounds (IV) which include new and known compounds useful medicinally as antibacterials or disinfectants at a dose of 0.1 to 10 g per kilogram body weight per a day for humans or warm-blooded animals when administered orally or by injection. The compounds are also useful as intermediates for the preparation of other useful compounds, e.g. cephalexin, by changing group A and/or group B by conventional methods.

REACTION IV: 3-METHYL-3-CEPHEM COMPOUNDS FROM 2'-HALOPENICILLIN COMPOUNDS

As is described in the section for Reaction II, heating a 2'-halopenicillin of formula

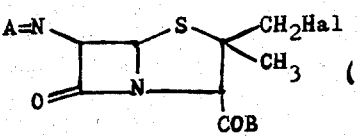

(Compound II)

wherein A, B, and Hal are as defined above, gives a 3-methyl-3-cephem compound of formula

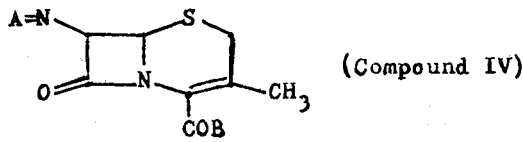

(Compound IV)

wherein A and B are as defined above, and a 3-halo-3-methylcepham compound III.

When the reaction temperature is high enough or heating is continued for a long enough time, the formation of Compound IV increases, and in many cases it becomes the sole product.

The temperature is usually higher than 50°C, and lower than 150°C. Preferable temperature is in the range of 90°C to 130°C. The reaction is preferably carried out in a solvent and, if required, in the presence of a psuedo-base e.g. urea or thiourea. Solvents be used include those cited in the section for Reaction II. Preferable solvents are dimethyl sulfoxide, N,N-dimethylformamide, N,N-dimethylacetamide, hexamethylphosphoramide, ethanol, and benzene. The presence of pseudo-base is not essential, the reaction being in fact cleaner and the reaction mixture easier to work up in the absence of stronger bases. The reaction solution may be stirred or kept under inert gas. The reaction is usually complete within 0.5 to 4 hours when the temperature is about 130°C. No detectable amount of the corresponding 2-cephem isomer has been found in the reaction mixture.

The products of this reaction are the same as those of Reaction III; they include new and known compounds useful medicinally as antibacterials or disinfectants, and as intermediates for the production of other useful compounds e.g. cephalexin.

REACTION V: DEPROTECTION OF AMINO-SUBSTITUENT A'

The amino-substituent (A') of the group A can be removed to give the corresponding amino compound by conventional methods. For example, the action of hydrazine on imide; the action of carbonium-ion forming reagents (nitrosyl chloride, N-bromosuccinimide, etc.) for penicillin N-side chain, acids (e.g. acid chlorides, boron trifluoride, toluene-p-sulfonic acid, or mineral acids), or the successive action of phosphorous pentahalide, alcohol, and diluted acids on amides. Hydrocarbon substituents cannot generally be removed, but some specific groups can. For example, treatment with an acid (e.g. toluene-p-sulfonic acid, formic acid, or acetic acid) removes a trityl, substituted trityl, 1-carbamoyl-1-propen-2-yl, or 1-carbalkoxy-1-propen-2-yl group; aniline salts remove a benzylidene group; hydrogenolysis removes trichloroethoxycarbonyl, benzyloxycarbonyl, trityl, substituted trityl, and like groups; and reduction removes 2-haloethoxycarbonyl, 2,2,2-trichloroethoxycarbonyl, benzhydryl, and like groups.

REACTION VI: DEPROTECTION OF CARBOXY-PROTECTING GROUP B

Suitable deprotection methods are known for each carboxy-protecting group (B') which can be removed without adverse effect on the rest of the molecule. For example, a 2-haloalkyl ester can be reduced with zinc, or by catalytic hydrogenation, if necessary after treatment with iodide; a 2-acyl-lower alkyl ester, oxymethyl esters, lower acylmethyl ester, α-lower acylbenzyl ester, aralkyl ester, imino-ester, phenyl ester, etc., can be hydrolyzed with base (e.g. sodium hydrogen carbonate, alkali metal carbonate, alkali metal hydroxide, alkali metal thiophenoxide); trityl ester, benzhydryl ester, and like esters can be hydrolyzed with acid (e.g. formic acid, acetic acid, mineral acid; or trifluoroacetic acid in the presence of anisole). Removal of a phenacyl group can be effected in high yield by ultra-violet ray irradiation; and benzyl ester, trityl ester, and substituted benzyl ester can be hydrogenolysed. An amide (e.g. N-alkoxyamide, N-hydroxyamide, saccharinimide, and like groups) can be cleaved with a base; and a salt of ester with a silicon or tin group, can be cleaved with acid.

REACTION VII: ACYLATION OF FREE AMINO GROUP A=N.

When the compounds II or III have an unsubstituted amino group as the group A=N, they can be acylated by conventional methods in the art. Such methods include the action of a carboxylic acid having the desired acyl group in the presence of a condensing reagent (e.g. carbodiimide or enzyme); the action of an acid anhydride, mixed anhydride, acid halide, reactive ester (e.g. phenyl esters, pyridyl esters, cyanomethyl ester, hydroxylamine ester), reactive amide (e.g. N-acylimidazole, N-acylphthalimide), azide, or other reactive derivative of the desired acid, preferably in the presence of a base.

REACTION VIII: PROTECTION OF THE CARBOXY GROUP

Compounds II or III with free carboxylic acid groups can be protected by conventional methods in the art. Such methods involve esterification (e.g. with an alcohol, halide, diazo-compound, halocarbonate, or the like, if necessary in the presence of a condensing reagent, all of which have desired groups to be introduced), amide formation (e.g. by the action of an amine or its reactive derivatives on the carboxylic acid or its ester), and salt formation (e.g. by replacement or by the action of a base, hexamethylsilazane, trimethyltin chloride).

A reactive group contained in Group A can be protected prior to the reactions and removed after the reaction by conventional methods in the art including hydrolysis of e.g. an ester, thioester, acetal, enol-ether, enamine, amide, or ketal, with an acid or base to recover e.g. a hydroxyl, thiol, ketone, aldehyde, amino, carboxyl, or sulfo; reduction of e.g. a trialkylsilylamino, tritylamino, or azide to recover an amino group; or other methods described in the sections on deprotection of the amino-substituent A and removal of the carboxy-protecting group B.

ISOLATION AND PURIFICATION OF THE PRODUCTS

The products of the processes can be isolated by conventional methods in the art, including extraction, precipitation, absorption, concentration, drying, counter-current distribution, treatment with an ion-exchange resin, crystallization, and lyophillization, and can be purified by recrystallization, fractional extraction, precipitation, chromatography on silica gel, salt formation and liberation, and like methods.

The following examples represent presently-preferred embodiments of this invention, but it is to be understood that the examples are given by way of illustration only and not of limitation. The elemental analyses of the compounds show good agreement with the calculated values.

Some of the examples are shown in Tables, in which following abbreviations are used.

Ac = acetyl
Bz = benzoyl
Di = dioxane
DMF = N,N-dimethylformamide
DMSO = dimethyl sulfoxide
Et = ethyl
HMPA = hexamethylphosphoramide
Lu = lutidine main = main product
Ms = methanesulfonyl
Nbz = p-nitrobenzoyl PhH = benzene
Py = pyridine
TLC = detected by thin-layer chromatography
To = toluene
Ts = toluene-p-sulfonyl
In the column of NMR spectra, the Hz values in parentheses show the coupling constants of signals Naming and numbering of the compounds are in accordance with those conventional for penicillins and cephalosporins.

EXAMPLE I-1.

A solution of benzhydryl 2,2-dimethyl-6β-(2,2,2-trichloroethoxycarbonylamino)penam-3α-carboxylate 1-oxide (2.0 g), benzoyl chloride (600 mg) and pyridine (340 mg) in toluene (120 ml) in a sealed glass tube is kept at 100°C for 2 hours 15 minutes. The reaction mixture is cooled and washed with aqueous sodium hydrogen carbonate and water. The dried solution is evaporated in vacuo to give a residue (2.7 g), which is then chromatographed over silica gel (150 g) utilizing 20% ether-petroleum ether as developing solvent, to give benzhydryl 2β-chloromethyl-2α-methyl-6β-(2,2,2-trichloroethoxycarbonylamino)penam-3α-carboxylate (970 mg; yield; 47%) as powder from rapidly eluted fractions. IR: $\nu_{max}^{CHCl_3}$ 1742, 1786 cm$^{-1}$.

EXAMPLE I-2 to 52

Using procedure similar to that in Example I-1, the following reactions are carried out with the variations specified. The results are illustrated in Table I-1. The available physical constants of the products are listed in Table I-2. The stereochemistry of some of the products was confirmed by X-ray crystallography and by nuclear Overhauser effect observations. All of the tabulated compounds have a 3α-COB and 6β-A=N group.

TABLE I-1

| Ex. No. | Halogen (Hal) | Starting material A=N | amount (mg) | B | Solvent (ml) | Base (mg) | Acid halide (mg) | Temp. (°C) Time (min.) | Yield (%) Crop (mg) | CH$_2$Hal position | Compound No. of product |
|---|---|---|---|---|---|---|---|---|---|---|---|
| 2 | Cl | Phenoxy-acetamido | (800) | Benzhydr-yloxy | To 50 | Py 145 | BzCl 250 | 100 110 | 40 330 | β | II-5 |
| 3 | Cl | Phenoxy-acetamido | (1000) | Benzhydr-yloxy | PhH 30 | Py 148 | NbzCl 348 | 80 90 | TLC main | β | II-5 |
| 4 | Cl | Phenoxy-acetamido | (250) | Benzhydr-yloxy | Di 15 | Py 45 | BzCl 79 | 100 60 | TLC main | β | II-5 |
| 5 | Cl | Phenoxy-acetamido | (250) | Benzhydr-yloxy | To 15 | Lu 60 | BzCl 79 | 100 120 | TLC main | β | II-5 |
| 6 | Cl | Phenoxy-acetamido | (250) | Benzhydr-yloxy | To 15 | NEt$_3$ 57 | BzCl 80 | 100 120 | TLC main | β | II-5 |
| 7 | Cl | Phenoxy-acetamido | (200) | Benzhydr-yloxy | To 15 | Py 33 | TsCl 79 | 100 120 | 20 — | β | II-5 |
| 8 | Cl | Phenoxy-acetamido | (100) | Benzhydr-yloxy | To 6 | Py 15 | AcCl 15 | 100 120 | TLC main | β | II-5 |
| 9 | Cl | Phenoxy-acetamido | (100) | Benzhydr-yloxy | To 6 | Py 15 | MsCl 216 | 100 120 | TLC main | β | II-5 |
| 10 | Cl | Phenoxy-acetamido | (500) | Cl$_3$CCH$_2$O— | To 25 | Py 80 | BzCl 141 | 100 120 | 43 223 | β | II-2 |
| 11 | Cl | Phenoxy-acetamido | (500) | Methoxy | To 20 | Py 104 | BzCl 185 | 100 120 | 72 290 | β | II-1 |
| 12 | Cl | Phenoxy-acetamido | (500) | p-Nitro-benzyloxy | To 25 | Py 79 | NbzCl 185 | 100 180 | TLC main | β | II-4 |

TABLE I-1-continued

| Ex. No. | Halogen (Hal) | Starting material A=N amount (mg) | B | Solvent (ml) | Base (mg) | Acid halide (mg) | Temp. (°C) Time (min.) | Yield (%) Crop (mg) | CH$_2$Hal position | Compound No. of product |
|---|---|---|---|---|---|---|---|---|---|---|
| 13 | Cl | Phenoxy-acetamido (100) | Trimethyl-silyloxy | To 6 | Py 29 | BzCl 34 | 100 120 | 23 24 | β | II-6 |
| 14 | Cl | Phenoxy-acetamido (500) | p-Bromophen-acyloxy | To 25 | Py 68 | BzCl 121 | 100 120 | 61 315 | β | II-3 |
| 15 | Cl | Phenoxy-acetamido (500) | Pivaloyloxy-methoxy | To 20 | Py 160 | BzCl 280 | 100 240 | 41 212 | β | |
| 16 | Cl | Phenoxy-acetamido (500) | Hydroxy | Di 45 | Py 374 | BzCl 365 | 100 120 | 26 135 | β | II-6 |
| 17 | Br | Phenoxy-acetamido (500) | Benzhydryl-oxy | To 20 | Py 82 | BzBr 192 | 100 180 | low — | β | |
| 18 | F | Phenoxy-acetamido (100) | Benzhydryl-oxy | To 6 | Py 15 | BzF 25 | 100 190 | low — | β | |
| 19 | Cl | Phenyl-acetamido (300) | Benzhydryl-oxy | To 12 | Py 46 | BzCl 82 | 110 90 | 30 100 | β | II-9 |
| 20 | Cl | Phenyl-acetamido (300) | Cl$_3$CCH$_2$O— | To 10 | Py 50 | BzCl 85 | 110 30 | 30 110 | β | II-7 |
| 21 | Cl | Phenyl-acetamido (500) | p-nitro-benzyloxy | To 50 | Py 79 | BzCl 42 | 100 120 | 29 130 | β | |
| 22 | Cl | Phenyl-acetamido (300) | p-nitro-benzyloxy | To 40 | Lu 64 | BzCl 84 | 110 100 | TLC main | β | |
| 23 | Cl | Phenyl-acetamido (1500) | Benzyloxy | To 150 | Py 320 | BzCl 570 | 100 140 | 37 580 | β | II-8 |
| 24 | Cl | Phenyl-acetamido (300) | Benzalamino-oxy | PhH 30 | Py 53 | NbzCl 123 | 80 60 | 6 21 | β | |
| 25 | Cl | C$_6$H$_5$CHCONH— <br> \| <br> NHCOO <br> \| <br> tert-C$_4$H$_9$ (100) | Benzhydryl-oxy | To 6 | Py 15 | BzCl 27 | 100 120 | 53 55 | β | II-10 |
| 26 | Cl | C$_6$H$_5$CHCONH— <br> \| <br> NHCOO <br> \| <br> tert-C$_4$H$_9$ (100) | Hydroxy | To 6 | Py 15 | BzCl 27 | 100 120 | TLC main | β | |
| 27 | Cl | C$_6$H$_5$CHCONH— <br> \| <br> NHCOCH$_3$ (100) | Methoxy | To 6 | Py 30 | BzCl 58 | 100 120 | 61 64 | β | |
| 28 | Cl | Benzoyl-amino (1000) | Benzhydryl-oxy | PhH 100 | Py 190 | BzCl 340 | 80 1320 | 4 42 | β | II-12 |
| 29 | Cl | (isoxazole structure) (870) | Benzhydryl-oxy | To 70 | Py 140 | BzCl 250 | 100 180 | 49 440 | β | II-13 |
| 30 | Cl | Phthalimido (3000) | Methoxy | PhH 140 | Py 630 | NbzCl 1480 | 80 120 | 40 1260 | α+β | II-14,*) II-15 |
| 31 | Cl | Phthalimido (300) | Methoxy | DMF 5 | Py 59 | NbzCl 148 | 130 60 | TLC — | α+β | II-14, II-15 |

TABLE I-1-continued

| Ex. No. | Halogen (Hal) | Starting material A=N amount (mg) | B | Solvent (ml) | Base (mg) | Acid halide (mg) | Temp. (°C) Time (min.) | Yield (%) Crop (mg) | CH$_2$Hal position | Compound No. of product |
|---|---|---|---|---|---|---|---|---|---|---|
| 32 | Cl | Phthalimido (10430) | Methoxy | PhH 1400 | Py 3150 | AcCl 3129 | 80 40 | 76 9000 | α+β | II-14, II-15 |
| 33 | Cl | Phthalimido (2700) | Phenacyloxy | PhH 30 | Py 512 | AcCl 500 | 80 45 | 28+ 21 780+600 | α+β | II-18, II-19 |
| 34 | Cl | Phthalimido (75) | Methoxy | PhH 2 | Py 16 | BzCl 28 | 80 22 | 32 25 | α+β | II-14, II-15 |
| 35 | Cl | Phthalimido (75) | Methoxy | PhH 2 | Py 16 | NbzCl 37 | 80 22 | 50 39 | α+β | II-14, II-15 |
| 36 | Cl | Phthalimido (75) | Methoxy | PhH 2 | Py 16 | Anisoyl chloride 34 | 80 22 | 38 30 | α+β | II-14, II-15 |
| 37 | Cl | Phthalimido (75) | Methoxy | PhH 2 | Py 16 | AcCl 16 | 80 22 | 64 50 | α+β | II-14, II-15 |
| 38 | Cl | Phthalimido (75) | Methoxy | PhH 2 | Py 16 | Pivaloyl chloride 24 | 80 22 | 48 38 | α+β | II-14, II-15 |
| 39 | Cl | Phthalimido (75) | Methoxy | PhH 2 | Py 16 | (COCl)$_2$ 25 | 80 22 | 30 24 | α+β | II-14, II-15 |
| 40 | Cl | Phthalimido (3800) | Methoxy | PhH 250 | Py 882 | AcCl 876 | 80 40 | 80 3010 | α+β | II-14, II-15 |
| 41 | Cl | Phthalimido (3000) | Benzyloxy | PhH 250 | Py 450 | AcCl 455 | 80 40 | 51 1600 | α+β | II-16 |
| 42 | Cl | Phthalimido (493) | Cl$_3$CCH$_2$O— | PhH 50 | Py 85 | AcCl 90 | 80 40 | 61 312 | α+β | II-17 |
| 43 | Cl | i—C$_4$H$_9$O$_2$CN— H (640) | Benzhydryl-oxy | To 25 | Py 80 | BzCl 170 | 100 120 | 52 348 | β | II-20 |
| 44 | Cl | Cl$_3$CCH$_2$OCN— ‖ OH (2000) | Benzhydryl-oxy | To 120 | Py 340 | BzCl 600 | 100 135 | 48 976 | β | II-21 |
| 45 | Cl | 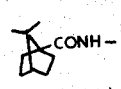 (100) | Benzhydryl-oxy | To 6 | Py 15 | BzCl 27 | 100 45 | 44 45 | β | |
| 46 | Cl |  (2700) | Benzhydryl-oxy | To 140 | Py 460 | BzCl 800 | 100 90 | 18 500 | β | II-11 |
| 47 | Cl | Salicyl-ideneamino (500) | Methoxy-methoxy | To 50 | Py 210 | BzCl 444 | 100 60 | 16 83 | ξ | II-22 |
| 48 | Cl | Salicyl-ideneamino (1000) | Benzhydryl-oxy | To 100 | Py 310 | BzCl 560 | 100 60 | 12 120 | ξ | II-23 |
| 49 | Cl | 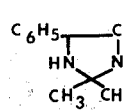 (100) | Anisyloxy | To 6 | Py 15 | BzCl 27 | 100 45 | 59 57 | α+β | |
| 50 | Cl | 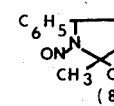 (840) | Benzhydryl-oxy | PhH 50 | Py 126 | AcCl 126 | 80 40 | 41 357 | ξ | II-24 |

TABLE I-1-continued

| Ex. No. | Halogen (Hal) | Starting material A=N amount (mg) | B | Solvent (ml) | Base (mg) | Acid halide (mg) | Temp. (°C) Time (min.) | Yield (%) Crop (mg) | CH₂Hal position | Compound No. of product |
|---|---|---|---|---|---|---|---|---|---|---|
| 51 | Cl | Tritylamino (100) | Benzhydryl-oxy | To 6 | Py 15 | BzCl 27 | 100 60 | 6 6 | β | |
| 52 | Cl | Phenoxy-acetamido (105) | Benzhydryl-oxy | To 7 | Py 16 | EtOOCCl 24 | 110 120 | 20 25 | β | II-5 |

*'Examples 30-37: The ratio of α to β -isomers is about 53 to 47, estimated from nuclear magnetic resonance spectrum.

TABLE I-2

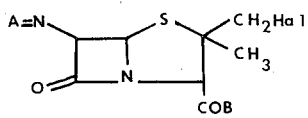

| Compound No. | Hal | A=N | B | CH₂Hal position | IR: CHCl₃ max (cm⁻¹) | NMR: δCDCl₃ (60 MHz) |
|---|---|---|---|---|---|---|
| II-1 | Cl | Phenoxy-acetamido | Methoxy | β | 1690, 1750, 1790. | 1.58s3H, 4.60s2H, 3.52s2H, 4.98s1H, 3.84s3H, 5.63–5.75m2H. |
| II-2 | Cl | Phenoxy-acetamido | Cl₃CCH₂O— | β | 1695, 1765, 1792. | 1.63s3H, 4.80s2H, 3.50s2H, 5.08s1H, 4.57s2H, 5.64–5.73m2H. |
| II-3 | Cl | Phenoxy-acetamido | p-Bromo-phenacyl-oxy | β | 1702, 1760, 1795. | |
| II-4 | Cl | Phenoxy-acetamido | p-Nitro-benzyloxy | β | 1692, 1750, 1790. | 1.51s3H, 5.05s1H, 3.46s2H, 5.33s2H, 4.60s2H, 5.66–5.77dd2H. |
| II-5 | Cl | Phenoxy-acetamido | Benzhydryl-oxy | β | 1692, 1743, 1788. | 1.30s3H, 5.03s1H, 3.44s2H, 6.95s1H, 4.57s2H, 5.32–5.50m2H. |
| II-6 | Cl | Phenoxy-acetamido | Hydroxy | β | 1695, 1730, 1780, 3440. | |
| II-7 | Cl | Phenylacet-amido | Cl₃CCH₂O— | β | 1660, 1762, 1781, 3250. | |
| II-8 | Cl | Phenyl-acetamido | Benzyloxy | β | 1680, 1746, 1788. | 1.38s3H, 4.89s1H, 3.28s2H, 5.13s2H, 3.57s2H, 5.54m2H. |
| II-9 | Cl | Phenyl-acetamido | Benzhydr-yloxy | β | 1680, 1745, 1788. | 1.28s3H, 4.97s1H, 3.27s2H, 5.61m2H, mp.115°C 3.62s2H, 6.91s1H. |
| II-10 | Cl | C₆H₄CHCONH— NHCOO tert-C₄H₉ | Benzhydryl-oxy | β | 1692, 1710, 1740, 1783. | 1.42s3H, 5.18d1H(7 Hz), 3.35s2H, 5.46–5.84m2H, 5.00s1H, 6.94s1H. |
| II-11 | Cl | Ketopinoyl-amino | Benzhydryl-oxy | β | 1670, 1733, 1785. | 3.64s2H, 1.00s,1.24s, and 5.14s1H, 1.36s(9H) 5.57–5.85m2H, 6.97s1H. |
| II-12 | Cl | Benzoylamino | Benzhydryl-oxy | β | 1674, 1741, 1789. | 1.37s3H, 5.80–5.95m2H, 3.67s2H, 7.00s1H, 5.10s1H, |
| II-13 | Cl | C₆H₅ ⟨isoxazole structure with CN, OH, CH₃⟩ | Benzhydryl-oxy | β | 1673, 1745, 1788. | 1.23s3H, 5.64dd1H(8;4Hz), 2.75s3H, 5.70d1H(4Hz), 3.00s2H, 6.18d1H(8Hz), 5.00s1H, 6.97s1H. |
| II-14 | Cl | Phthalimido | Methoxy | β | 1730, 1780, 1798. | 1.60s3H, 4.50d1H(12Hz), 3.70d1H(12Hz), 5.20s1H, 3.82s3H, 5.72m2H. mp. 108° |
| II-15 | Cl | Phthalimido | Methoxy | α | 1730, 1780, 1798. | 1.94s3H, 4.77s1H, 3.82s3H, 5.65m2H. 3.85s2H, mp. 165°. |

TABLE I-2-continued

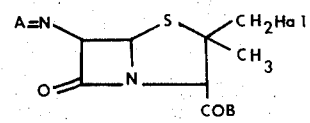

| Compound No. | Hal | A=N | B | CH$_2$Hal position | IR: $\nu_{max}^{CHCl_3}$ (cm$^{-1}$) | NMR: $\delta$CDCl$_3$ (60 MHz) |
|---|---|---|---|---|---|---|
| II-16 | Cl | Phthalimido | Benzyloxy | α + β | 1730–1740, 1780, 1798. | |
| II-17 | Cl | Phthalimido | Cl$_3$CCH$_2$O— | α + β | 1730, 1773, 1805. | |
| II-18 | Cl | Phthalimido | Phenacyl-oxy | β | 1710, 1730, 1750, 1775, 1795. | 1.78s3H, 5.56s2H, 4.13ABq(12Hz), 5.77s2H, 5.26s3H, 7.9–7.4m9H. |
| II-19 | Cl | Phthalimido | Phenacyl-oxy | α | 1710, 1730, 1755, 1780, 1805. | 2.00s3H, 5.5ABq2H(10Hz), 4.07s2H, 5.66s2H, 4.98s1H, 7.9–7.4m9H. |
| II-20 | Cl | i—C$_4$H$_9$OOCNH— | Benzhydryl-oxy | β | 1730, 1785. | 0.92d6H(6.5Hz), 5.05s1H, 1.35s3H, 5.45–5.68m2H, 3.59s2H, 6.94s1H, 3.88d2H(6.5Hz), |
| II-21 | Cl | Cl$_3$CCH$_2$OOCNH— | Benzhydryl-oxy | β | 1742, 1786. | 1.37s3H, 5.47dd1H(8;4Hz), 3.64s2H, 5.75d1H(4Hz), 4.76s2H, 6.07d1H(8Hz), 5.11s1H, 7.00s1H. |
| II-22 | Cl | 2-HO-C$_6$H$_4$-CH=N— | CH$_3$OCH$_2$O— | ξ | 1629, 1750, 1780. | 1.66s3H, 5.35d1H(4Hz), 3.57s2H, 5.38s2H, 3.66s2H, 5.84d1H(4Hz), 5.14s1H, 8.65s1H. |
| II-23 | Cl | 2-HO-C$_6$H$_4$-CH=N— | Benzhydryl-oxy | ξ | 1630, 1742, 1780. | 1.37s3H, 5.20s1H, 3.14s2H, 5.76d1H(4Hz), 5.15d1H(4Hz), 8.55s1H. |
| II-24 | Cl | C$_6$H$_5$, CH$_3$, CH$_3$ hydantoin-N— | Benzhydryl- | α | — | 1.67s3H, 4.73s1H, 2.07s3H, 4.87d1H(4Hz), 2.10s3H, 5.43s1H, 3.55s2H, 5.63d1H(4Hz), 6.92s1H. |

EXAMPLE II-1.

A solution of benzhydryl 2β-chloromethyl-2α-methyl-6β-(α-tert-butoxycarbonylaminophenylacetamido)penam-3α-carboxylate (180 mg) in dimethyl sulfoxide (4 ml) is heated at 100°C for 2 hours. The reaction mixture is poured into ice water and extracted with ethyl acetate. The extract solution is washed with 3% aqueous sodium hydrogen carbonate, and water, dried over sodium sulfate, and evaporated to give crude product (155 mg), which is purified by chromatography over silica gel (10 g), using 30% ether-petroleum ether as developing solvent, to give thin-layer chromatographically pure benzhydryl 3β-chloro-3α-methyl-7β-(α-tert-butoxycarbonylaminophenylacetamido)cepham-4α-carboxylate (130 mg; Yield: 72.3%). IR: $\nu_{max}^{CHCl_3}$ 1780, 1740, 1708, 1690 cm$^{-1}$.

EXAMPLE II-2 to 24.

Using a procedure similar to that in Example II-1, the following reactions are carried out with the variations specified. The results are illustrated in Table II-1. The available physical constants of the products are also listed in Table II-2. The stereochemistry of some of the products was confirmed by X-ray crystallography and by nuclear Overhauser effect observations. All of the tabulated compounds have a 3β-halogen, 4α-COB group, and 7β-A=N group.

TABLE II-1

| Ex. No. | Starting material | | | Solvent (ml) | Temp. (°C) Time (min.) | Yield (%) Crop (mg) | Compound No. of product |
|---|---|---|---|---|---|---|---|
| | Hal | A=N Amount (mg) | B | | | | |
| 2 | Cl | Phenoxy-acetamido (200) | Benzhydryl-oxy | DMSO 15 | 100 120 | 100 200 | III-3 |
| 3 | Cl | Phenoxy-acetamido (500) | Cl₃CCH₂O— | DMSO 13 | 100 120 | 40*⁾ 200 | III-1 |
| 4 | Cl | Phenoxy-acetamido (100) | Methoxy | DMF 6 | 100 240 | 95 95 | |
| 5 | Cl | Phenoxy-acetamido (200) | p-Nitro-benzyloxy | DMSO 3 | 90 120 | TLC main | |
| 6 | Cl | Phenoxy-acetamido (250) | p-Bromo-phenacyloxy | DMSO 15 | 100 120 | 92 230 | III-2 |
| 7 | Cl | Phenoxy-acetamido (150) | Pivaloyloxy-methoxy | DMSO 15 | 90 120 | 95 142 | |
| 8 | Cl | Phenoxy-acetamido (100) | Hydroxy | Di 10 | 100 90 | 20 20 | |
| 9 | F | Phenoxy-acetamido (10) | Benzhydryl-oxy | DMSO 1 | 90 180 | TLC main | |
| 10 | Cl | Phenyl-acetamido (120) | Benzhydryl-oxy | DMSO 10 | 100 120 | 100 121 | III-4 |
| 11 | Cl | Phenyl-acetamido (300) | Cl₃CCH₂O— | DMSO 10 | 90 180 | 83 250 | |
| 12 | Cl | Phenyl-acetamido (20) | p-Nitro-benzyloxy | DMSO 1 | 90 100 | TLC main | |
| 13 | Cl | Phenyl-acetamido (20) | Benzalamino-oxy | HMPA 1 | 90 100 | TLC main | |
| 14 | Cl | Phenyl-acetamido (300) | Methoxy | DMSO 8 | 90 120 | 20 60 | |
| 15 | Cl | Phthalimido (75) | Methoxy | DMF 3 | 100 120 | 28 20 | III-5 |
| 16 | Cl | Phthalimido (11) | Methoxy | DMSO+H₂O 0.5 12 | 90 120 | TLC main | III-5 |
| 17 | Cl | Norbornyl-carboxamido (50) | Benzhydryl-oxy | DMSO 1 | 100 150 | 90 45 | |
| 18 | Cl | Ketopinoyl-amino (1990) | Benzhydryl-oxy | DMSO 70 | 100 120 | 85 1700 | III-6 |
| 19 | Cl | C₆H₅CHCONH—<br>    |<br>    NHCOO<br>        |<br>        tert-C₄H₉ (400) | Benzhydryl-oxy | DMSO 10 | 100 90 | 90 358 | III-7 |
| 20 | Cl | 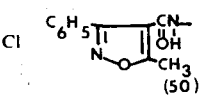 (50) | Benzhydryl-oxy | DMSO 5 | 100 80 | 100 50 | III-8 |
| 21 | Cl | i—C₄H₉O₂CNH— (90) | Benzhydryl-oxy | DMSO 10 | 100 120 | 88 79 | III-9 |
| 22 | Cl | Tritylamino (20) | Benzhydryl-oxy | DMSO 3 | 100 300 | 10 19 | |
| 23 | Cl | 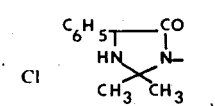 (100) | Benzhydryl-oxy | DMSO 8 | 100 120 | 75 75 | |
| 24 | Cl | 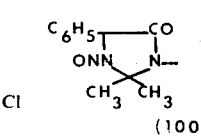 (100) | Benzhydryl-oxy | DMSO 8 | 100 120 | 80 80 | III-10 |

*Example 3: The product is a by-product of Example IV-3 i.e. Compounds III-1 and IV-2 formed simultaneously by the reaction.

TABLE II-2

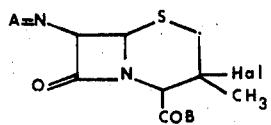

| Compound No. | Hal | A=N | B | IR: $\nu_{max}^{CHCl_3}$ (cm$^{-1}$) | NMR: $\delta CDCl_3$ (60MHz) |
|---|---|---|---|---|---|
| III-1 | Cl | Phenoxyacetamido | Cl$_3$CCH$_2$O— | 1695, 1760, 1782. | 1.80s3H, 4.83s1H, 2.77d1H(14Hz), 4.93d2H(2Hz), 3.70d1H(14Hz), 5.38d1H(5Hz). |
| III-2 | Cl | Phenoxyacetamido | p-Bromophenacyloxy | 1703, 1753, 1779. | 4.59s2H, 5.85dd1H(5;10Hz). 1.97s3H, 4.95s1H, 2.80d1H(14Hz), 5.40d1H(4Hz), 3.90d1H(14Hz), 5.48s2H, |
| III-3 | Cl | Phenoxyacetamido | Benzhydryloxy | 1697, 1741, 1782. | 4.62s2H, 5.78dd1H(4;10Hz). 1.50s3H, 5.27d1H(4Hz), 2.62d1H(15Hz), 4.86s1H, 3.61d1H(15Hz), |
| III-4 | Cl | Phenylacetamido | Benzhydryloxy | 1683, 1739, 1776. | 4.38s2H, 5.67dd1H(4;10Hz). 1.47s3H, 5.17d1H(4Hz), 2.57d1H(14Hz), 4.78s1H, 3.58d1H(14Hz), 6.89s1H, 3.62s2H, 5.63dd1H(4;10Hz), 6.40d1H(10Hz). |
| III-5 | Cl | Phthalimido | Methoxy | 1730, 1775, 1790. | 1.77s3H, 4.94s1H, 3.04d1H(15Hz),5.37d1H(5Hz), 3.45d1H(15Hz),5.60d1H(5Hz). 3.80s3H, mp. 193-5° |
| III-6 | Cl | Ketopinoylamino | Benzhydryloxy | 1670, 1735, 1775. | 1.00s3H, 4.83s1H, 1.20s3H, 5.20d1H(4Hz), 1.47s3H, 5.69dd1H(9;4Hz), 2.61d1H(14Hz), 6.87s1H, 3.57d1H(14Hz), 7.35s1H. |
| III-7 | Cl | C$_6$H$_5$CHCONH—<br>\|<br>NHCOO<br>\|<br>tert-C$_4$H$_9$ | Benzhydryloxy | 1690, 1708, 1740, 1780. | 1.40s9H, 5.14d1H(4Hz), 2.50d1H(15Hz), 5.27s1H, 3.52d1H(15Hz), 6.87s1H, 4.83s1H, 5.60dd1H(10;4Hz). |
| III-8 | Cl | C$_6$H$_5$-isoxazole-CNH—<br>CH$_3$ | Benzhydryloxy | 1670, 1745, 1778. | 1.42s3H, 5.20d1H(4Hz), 2.50d1H(14Hz), 4.75s1H, 2.79s3H, 5.68dd1H(10;4Hz), 3.57d1H(14Hz), 6.90s1H. |
| III-9 | Cl | i—C$_4$H$_9$OOCNH— | Benzhydryloxy | 1731, 1780. | 0.93d6H(7Hz), 4.84s1H, 1.49s3H, 5.23d1H(4Hz), 1.49–2.11m1H, 5.40–5.64m2H, 2.63d1H(14Hz), 6.88s1H. 3.62d1H(14Hz), |
| III-10 | Cl | C$_6$H$_5$-oxadiazinone ON CH$_3$ CH$_3$ | Benzhydryloxy | 1736, 1793. | 1.30s3H, 4.85d1H(4Hz), 1.83s3H, 5.11s1H, 2.06s3H, 5.45s1H, 3.36d1H(12Hz), 5.76d1H(4Hz), 4.08d1H(12Hz), 6.94s1H. |

EXAMPLE III-1.

A solution of benzhydryl 3β-chloro-3α-methyl-7β-phenoxyacetamidocepham-4α-carboxylate (180 mg) in dimethyl sulfoxide (5 ml) is heated at 130°C for 4 hours. The reaction mixture is poured into ice water and extracted with ethyl acetate. The extract solution is washed with aqueous sodium hydrogen carbonate and water, dried over sodium sulfate and evaporated to remove the solvent. The residue is benzhydryl 3-methyl-7β-phenoxyacetamido-3-cephem-4-carboxylate (140 mg; Yield: 83.4%). IR: $\nu_{max}^{CHCl_3}$ 1785, 1727, 1695 cm$^{-1}$.

EXAMPLES III-2 to 21.

Using a procedure similar to that in Example III-1, the following reactions are carried out with the variations specified. The results are illustrated in Table III-1. The available physical constants of the products are also listed in Table III-2. All of the tabulated compounds have 7β-A=N group.

TABLE III-1

| Ex. No. | Starting material | | | Solvent (ml) | Temp. (°C) Time (min.) | Yield (%) Crop (mg) | Compound No. of product |
|---|---|---|---|---|---|---|---|
| | Hal | A=N Amount (mg) | B | | | | |
| 2 | Cl | Phenoxy-acetamido (180) | Benzhydryl-oxy | DMSO 5 | 130 240 | 83 140 | IV-3 |
| 3 | Cl | Phenoxy-acetamido (4000) | $Cl_3CCH_2O$— | DMSO 60 | 100 120 | 90 3360 | IV-2 |
| 4 | Cl | Phenoxy acetamido (50) | Methoxy | DMSO 1 | 140 120 | TLC main | IV-1 |
| 5 | Cl | Phenoxy-acetamido (50) | p-Nitro-benzyloxy | DMF 3 | 130 120 | TLC main | IV-4 |
| 6 | Cl | Phenoxy-acetamido (100) | Trimethyl-silyloxy | DMSO 5 | 130 120 | 88 67 | IV-7 |
| 7 | Cl | Phenoxy-acetamido (150) | p-Bromo-phenacyloxy | DMSO 7 | 130 120 | 78 110 | IV-5 |
| 8 | Cl | Phenoxy-acetamido (200) | Pivaloyloxy-methoxy | DMSO 10 | 100 60 | 85 157 | IV-6 |
| 9 | Cl | Phenoxy-acetamido (150) | Hydroxy | Di 10 | 90 120 | 78 106 | IV-7 |
| 10 | Cl | Phenyl-acetamido (50) | $Cl_3CCH_2O$— | DMSO 5 | 130 60 | 93 43 | IV-8 |
| 11 | Cl | Phenyl-acetamido (10) | p-Nitro-benzyloxy | DMSO 3 | 130 60 | TLC main | |
| 12 | Cl | $C_6H_5\underset{NHCOO}{\overset{|}{C}}HCONH-$ tert-$C_4H_9$ (100) | Benzhydryl-oxy | DMSO 10 | 100 60 | TLC main | IV-10 |
| 13 | Cl | $C_6H_5\underset{NHCOO}{\overset{|}{C}}HCONH-$ tert-$C_4H_9$ (150) | Hydroxy | DMSO 9 | 130 120 | 82 110 | IV-11 |
| 14 | Cl | $C_6H_5\underset{NHCOCH_3}{\overset{|}{C}}HCONH-$ (200) | Methoxy | DMSO 10 | 90 120 | 73 133 | IV-12 |
| 15 | Cl | Phthalimido (30) | Methoxy | DMSO 1 | 130 60 | TLC main | IV-16 |
| 16 | Cl | 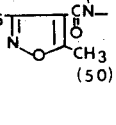 (50) | $Cl_3CCH_2O$— | DMSO 5 | 130 120 | 85 40 | IV-15 |
| 17 | Cl | 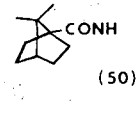 (50) | Benzhydryl-oxy | DMSO 3 | 120 110 | 92 44 | |
| 18 | Cl | 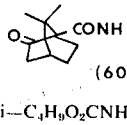 (600) | Benzhydryl-oxy | DMSO 35 | 135 120 | 71 400 | IV-13 |
| 19 | Cl | i—$C_4H_9O_2CNH$— (50) | Benzhydryl-oxy | DMSO 3 | 100 60 | 42 84 | IV-14 |
| 20 | Cl | Tritylamino (100) | Benzhydryloxy | DMSO 5 | 70 240 | 45 47 | |
| 21 | Cl | 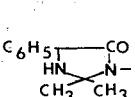 (200) | Benzalamino-oxy | DMSO 10 | 120 100 | 78 145 | |

TABLE III-1-continued

| Ex. No. | Hal | Starting material A=N | B | Solvent (ml) | Temp. (°C) Time (min.) | Yield (%) Crop (mg) | Compound No. of product |
|---|---|---|---|---|---|---|---|
| | | Amount (mg) | | | | | |
| 22*) | Cl | Phenoxy-acetamido (100) | Cl₃CCH₂O— | DMF 5 | 100 120 | 92 86 | IV-2 |
| 23*) | Cl | Phenyl-acetamido (500) | Benzhydryl-oxy | DMSO 20 | 100 210 | 75 350 | IV-9 |
| 24*) | Cl | i—C₄H₉OOCNH— (50) | Benzhydryl-oxy | DMSO 3 | 100 60 | 42 84 | IV-14 |

*)Examples 22 to 24 are carried out in the presence of pseudo-base. Example 22: thiourea (10mg); Example 23: urea(90mg); Example 24: urea (5 mg).

TABLE III-2

[Structure: A=N attached to a β-lactam fused bicyclic system with S, CH₃, and COB groups]

| Compound No. | Hal | A=N | B | IR: $\eta_{max}^{CDCl_3}$ (cm⁻¹) | NMR: $\delta CDCl_3$ (60MHz) |
|---|---|---|---|---|---|
| IV-1 | Cl | Phenoxy-acetamido | Methoxy | 1689, 1721, 1785. | 2.16s3H. mp. 139°C. |
| IV-2 | Cl | Phenoxy-acetamido | Cl₃CCH₂O— | 1695, 1741, 1780. | 2.21s3H, 4.90d2H(3Hz), 3.25d1H(18Hz), 5.05d1H(5Hz), 3.52d1H(18Hz), 5.64–5.98m2H, 4.56s2H, mp. 119°. |
| IV-3 | Cl | Phenoxy-acetamido | Benzhydryl-oxy | 1695, 1727, 1785. | 2.14s3H, 5.04d1H(5Hz), 3.20d1H(18Hz), 5.86dd1H, 3.47d1H(18Hz), (10;5Hz) 4.59s2H, 7.00s1H. mp. 152°. |
| IV-4 | Cl | Phenoxy-acetamido | p-Nitro-benzyl-oxy | 1691, 1727, 1783. | 2.21s3H. mp. 193° |
| IV-5 | Cl | Phenoxy-acetamido | p-Bromo-phenacyl-oxy | 1698, 1755, 1780. | |
| IV-6 | Cl | Phenoxy-acetamido | Pivaloyl-oxymethoxy | 1695, 1752, 1780. | |
| IV-7 | Cl | Phenoxy-acetamido | Hydroxy | 1692, 1750, 1792. | 2.10s3H. mp. 187° |
| IV-8 | Cl | Phenyl-acetamido | Cl₃CCH₂O— | 1682, 1748, 1785. | 2.07s3H. mp. 161° |
| IV-9 | Cl | Phenyl-acetamido | Benzhydryl-oxy | 1682, 1730, 1785. | 2.05s3H. |
| IV-10 | Cl | C₆H₅CHCONH—<br>    \|<br>  NHCOO<br>    \|<br>  tert-C₄H₉ | Benzhydryl-oxy | 1695, 1723, 1780. | 1.56s9H, 5.14d1H(5Hz), 2.00s3H, 5.47–6.00m2H, 3.07d1H(18Hz), 6.93s1H. 3.34d1H(18Hz), 4.90d1H(4Hz), |
| IV-11 | Cl | C₆H₅CHCONH—<br>    \|<br>  NHCOO<br>    \|<br>  tert-C₄H₉ | Hydroxy | 1629, 1752, 1790. | 2.10s3H. mp. 135° |
| IV-12 | Cl | C₆H₅CHCONH—<br>    \|<br>  NHCOCH₃ | Methoxy | 1640, 1680, 1730, 1775. | 1.9s3H. |
| IV-13 | Cl | Ketopinoyl-amino | Benzhydryl-oxy | 1673, 1732, 1782. | 1.01s3H, 4.97d1H(5Hz), 1.28s3H, 5.80dd1H(8;5Hz), 2.10s3H, 6.91s1H. 3.30d2H(4Hz), |
| IV-14 | Cl | i—C₄H₉OOCNH— | Benzhydryl-oxy | 3350. 1729, 1775, 3475. | 0.93d6H(7Hz), 3.93d2H(7Hz), 1.60–1.93m1H, 4.93d1H(5Hz), 2.09s3H, 5.40–5.71m2H, 3.29d2H(4Hz), 6.93s1H. |

TABLE III-2-continued

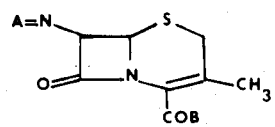

| Compound No. | Hal | A=N | B | IR: $\eta_{max}^{CDCl_3}$ (cm$^{-1}$) | NMR: $\delta CDCl_3$ (60MHz) |
|---|---|---|---|---|---|
| IV-15 | Cl | C$_6$H$_5$-, C-N-, OH, N-O, CH$_3$ | Cl$_3$CCH$_2$O— | 1670, 1740, 1785 | 2.18s3H, 4.93d1H(5Hz), 2.74s3H, 5.80dd1H(10;5Hz), 3.09d1H(18Hz), 6.16d1H(10Hz), 3.38d1H(18Hz), 6.83s1H, 4.84d2H(3Hz), |
| IV-16 | Cl | Phthalimido | Methoxy | 1730, 1780 | 2.33s3H, 5.13d1H(4Hz), 2.97d1H(15Hz), 5.77d1H(4Hz), 3.76d1H(15Hz), 7.63–8.10m4H, 3.86s3H, |

EXAMPLE IV-1.

A solution of 2,2,2-trichloroethyl 2β-chloromethyl-2α-methyl-6β-phenoxyacetamidopenam-3α-carboxylate (277 mg) in dimethyl sulfoxide (5 ml) is heated at 100°C for 1 hour, and then at 130°C for 1 hour. The reaction mixture is poured into iced water, and extracted with ether. The extract solution is washed with aqueous sodium hydrogen carbonate, and water, and dried over sodium sulfate. Evaporation of the dried solution gives 2,2,2-trichloroethyl 3-methyl-7β-phenoxyacetamido-3-cephem-4-carboxylate (214 mg; Yield: 83%) as colorless powder. IR: $\nu_{max}^{CHCl_3}$ 1780, 1741, 1695 cm$^{-1}$.

EXAMPLE IV-2 to 22.

Using a procedure similar to that in Example IV-1, the following reactions are carried out with the variations specified. The results are illustrated in Table IV-1. The available physical constants of the products are also listed in Table III-2. All of the tabulated compounds have a 7β-A=N group.

TABLE IV-1

| Ex. No. | Starting material | | | Solvent (ml) | Temp. (°C) | Yield (%) | Compound No. of product |
|---|---|---|---|---|---|---|---|
| | Hal | A=N Amount (mg) | B | | Time (min.) | Crop (mg) | |
| 2 | Cl | Phenoxy-acetamido (500) | Benzhydryl-oxy | DMSO 20 | 130 120 | 98 460 | IV-3 |
| 3 | Cl | Phenoxy-acetamido (500) | Cl$_3$CCH$_2$O— | DMSO 13 | 100 120 | 40 190 | IV-2 |
| 4 | Cl | Phenoxy-acetamido (500) | Methoxy | DMSO 10 | 130 120 | 93 423 | IV-1 |
| 5 | Cl | Phenoxy-acetamido (100) | p-Nitro-benzyloxy | DMSO 10 | 110 120 | 81 74 | IV-4 |
| 6 | Cl | Phenoxy-acetamido (250) | p-Bromo-phenacyloxy | HMPA 10 | 130 80 | 86 201 | IV-5 |
| 7 | Cl | Phenoxy-acetamido (250) | Pivaloyloxy-methoxy | DMF 10 | 130 120 | 91 210 | IV-6 |
| 8 | Cl | Phenoxy-acetamido (300) | Benzhydryl-oxy | DMSO 10 | 110 60 | 89 232 | IV-3 |
| 9 | Cl | Phenoxy-acetamido (150) | Hydroxy | Di 10 | 90 120 | 96 132 | IV-7 |
| 10 | Cl | Phenyl-acetamido (53) | Benzhydryl-oxy | DMSO 1 | 90 60 | TLC main | IV-9 |
| 11 | Cl | Phenyl-acetamido (100) | Cl$_3$CCH$_2$O— | DMSO 5 | 130 60 | 89 83 | IV-8 |
| 12 | Cl | Phenyl-acetamido (162) | p-Nitro-benzyloxy | DMSO 7 | 110 120 | TLC main | |
| 13*) | Cl | C$_6$H$_5$CHCONH—, NHCOO, tert-C$_4$H$_9$ (50) | Benzhydryl-oxy | DMSO 4 | 130 70 | 100 47 | IV-10 |

TABLE IV-1-continued

| Ex. No. | Starting material | | | Solvent (ml) | Temp. (°C) Time (min.) | Yield (%) Crop (mg) | Compound No. of product |
|---|---|---|---|---|---|---|---|
| | Hal | A=N Amount (mg) | B | | | | |
| 14**) | Cl | C₆H₅CHCONH—<br>    |<br>   NHCOO<br>    |<br>   tert-C₄H₉<br>(500) | Hydroxy | EtOH 20 | 78 75 | 84 375 | IV-11 |
| 15 | Cl | C₆H₅CHCONH—<br>    |<br>   NHCOCH₃<br>(500) | Methoxy | DMSO 10 | 130 120 | 81 372 | IV-12 |
| 16 | Cl | 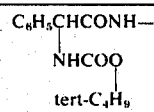<br>(52) | Benzhydryl-oxy | DMSO 1 | 130 60 | 95 43 | |
| 17 | Cl | 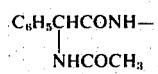<br>(10) | Benzhydryl-oxy | DMSO 1 | 100 45 | TLC main | IV-13 |
| 18 | Cl | Phthalimido<br>(50) | Methoxy | DMSO 1 | 130 60 | 95 43 | IV-16 |
| 19 | Cl | 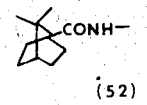<br>(50) | Benzhydryl-oxy | DMSO 1 | 100 90 | TLC main | IV-15 |
| 20 | Cl | i—C₄H₉O₂CNH—<br>(230) | Benzhydryl-oxy | DMSO 6 | 100 120 | 92 197 | IV-14 |
| 21 | Cl | Tritylamino<br>(230) | Benzhydryl-oxy | DMSO 10 | 100 75 | 73 160 | |
| 22 | Cl | 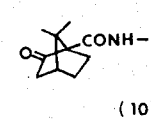<br>(300) | Benzalamino-oxy | DMSO+PhH 5 5 | 80 60 | 93 253 | |

*)Example 13: in the presence of urea (5 mg).
**)Example 14: in the presence of thiourea (109 mg).

EXAMPLE V-1.

A solution of benzhydryl 2-chloromethyl-2-methyl-6-phenoxyacetamidopenam-3-carboxylic acid (2.76 g) in benzene (100 ml) is heated at 60°C in the presence of pyridine (10 ml) and phosphorous pentachloride (1.51 g) for 2 hours. The reaction mixture is concentrated under reduced pressure, and the residue is dissolved in methanol (200 ml) and kept at room temperature overnight. The solution is concentrated in vacuo to remove methanol, and the residue is dissolved in 50 % aqueous tetrahydrofuran (50 ml). After 15 minutes, the mixture is concentrated to remove tetrahydrofuran, The residual solution is neutralized with 1 N sodium hydroxide, and extracted with ethyl acetate. The extract solution is dried over sodium sulfate, concentrated to 50 ml, and kept at 0°C overnight. The separated crystals are collected to give benzhydryl 6-amino-2-chloromethyl-2-methylpenam-3α-carboxylate (1.57 g).

EXAMPLE V-2.

To a solution of benzhydryl 6β-benzalamino-2ξ-chloromethyl-2ξ-methylpenam-3α-carboxylate (500 mg) in methanol (10 ml) is added aniline hydrochloride (142 mg) under ice cooling, and the mixture is stirred at room temperature for 1 hour. Evaporation of the reaction mixture affords a residue, which is dissolved in ether. The solution is washed with water and dilute hydrochloric acid, dried over sodium sulfate, and evaporated to remove the solvent. The residue is benzhydryl 6β-amino-2ξ-chloromethyl-2ξ-methylpenam-3α-carboxylate (266 mg).

EXAMPLE V-3.

To a solution of 2,2,2-trichloroethyl 3β-chloro-3α-methyl-7β-phenoxyacetamidocepham-4α-carboxylate (2.29 g) in benzene (130 ml) is added pyridine (10 ml) and the mixture is cooled at −60°C in the presence of phosphorous pentachloride (1.51 g) for 2 hours. The reaction mixture is evaporated in vacuo to remove benzene, methanol (250 ml) is added thereto, and the solution kept at room temperature overnight. The solution is concentrated to give a residue which is dissolved in 50% aqueous tetrahydrofuran (50 ml), and the tetrahydrofuran is evaporated after 15 minutes. The residual solution is neutralized with 1N sodium hydroxide, and evaporated to give 2,2,2-trichloroethyl 7β-amino-3β-chloro-3α-methylcepham-4α-carboxylate (1.53 g).

EXAMPLE V-4.

A solution of p-nitrobenzyl 3β-chloro-3α-methyl-7β-phenoxyacetamidocepham-4α-carboxylate (100 mg) and toluene-p-sulfonic acid monohydrate (75 mg) in methanol (20 ml) is refluxed for 6 hours. The reaction mixture is concentrated to 5 ml, and diluted with ether. The separated crystals are collected by filtration, washed with methanol and ether, and dried to give p-nitrobenzyl 7β-amino-3β-chloro-3α-methylcepham-4α-carboxylate p-toluenesulfonic acid salt. (78 mg).

EXAMPLE V-5.

A solution of benzhydryl 7β-(1-carbethoxy-1-propen-2-ylamino)-3β-chloro-3α-methylcepham-4α-carboxylate (107 mg) and 1N hydrochloric acid (0.1 ml) in a mixture of chloroform and acetone (1:1; 2 ml) is stirred at room temperature for 1 hour. The reaction mixture is washed with water, dried, and evaporated to remove the solvent. The residue is treated with a mixture of ether and petroleum ether to give solid benzhydryl 7β-amino-3β-chloro-3α-methylcepham-4α-carboxylate (60 mg).

EXAMPLE V-6.

To a solution of benzhydryl 3β-chloro-3α-methyl-7β-phenoxyacetamidocepham-4α-carboxylate (175 mg) in bezene (10 ml) is added pyridine (38 mg) and phosphorous pentachloride (100 mg), and the mixture is stirred at −65°C for 2 hours under nitrogen gas. After removal of benzene, methanol (20 ml) is added to the reaction mixture, and kept in a refrigerator for two days. Then the mixture is evaporated to remove methanol, and the residue is dissolved in aqueous dioxane (1:2) at room temperature, and neutralized to pH 7.0 with diluted sodium hydroxide. The solution is extracted with ethyl acetate, dried and concentrated to 5 ml, and mixed with toluene-p-sulfonic acid monohydrate (61 mg) in ethyl acetate. After 13 hours, the precipitate is collected by filtration and dried to give benzhydryl 3β-chloro-3α-methyl-7β-aminocepham-4α-carboxylate toluene-p-sulfonate (120 mg; Yield: 66%). IR: $\nu_{max}^{CHCl_3}$ 1785, 1738, 1240 cm$^{-1}$.

EXAMPLE V-7.

To a solution of benzhydryl 7β-benzyloxycarbonylamino-3β-chloro-3-methylcepham-4α-carboxylate (110 mg) in ethanol (10 ml) is added previously reduced 5% palladium charcoal (50 mg), and the mixture is shaken under hydrogen gas. After 60 minutes, the reaction mixture is filtered, and the filtrate is evaporated. The residue is treated with a mixture of ether and petroleum ether to give solid benzhydryl 7β-amino-3β-chloro-3α-methylcepham-4α-carboxylate (52 mg).

EXAMPLE V-1.

To a solution of p-nitrobenzyl 2β-chloromethyl-2α-methyl-6β-phenoxyacetamidopenam-3α-carboxylate (520 mg) in ethyl acetate (15 ml) is added previously reduced 10% palladium charcoal (400 mg) and the mixture is shaken under hydrogen gas for 30 minutes. The ceaction mixture is filtered to remove solid, and the filtrate is concentrated to give a residue of 2β-chloromethyl- 2α-methyl-6β-phenoxyacetamidopenam-3α-carboxylic acid (314 mg).

EXAMPLE VI-2.

A solution of p-nitrobenzyl 2β-chloromethyl-2α-methyl-6β-phenoxyacetamidopenam-3α-carboxylate (1 g) and potassium thiophenoxide (0.29 g) in dimethylformamide (1.5 ml) is kept at room temperature for 45 minutes. The reaction mixture is diluted with a mixture of acetone and ether (1:1), and separated crystals are collected by filtration to give potassium 2β-chloromethyl-2α-methyl-6β-phenoxyacetamidopenam-3α-carboxylate (610 mg).

EXAMPLE VI-3.

To a solution of 2,2,2-trichloroethyl 2β-chloromethyl-2α-methyl-6β-phenoxyacetamidopenam-3α-carboxylate (400 mg) and acetic anhydride (1.6 ml) in dimethylformamide (8 ml) is added zinc metal (272 mg) under ice cooling, and the mixture is stirred for 1.5 hours. The reaction mixture is filtered, and the solid is washed with ethyl acetate and water. The combined filtrate and washings are shaken together, and the ethyl acetate layer is separated, adjusted with hydrochloric acid to pH 3, then extracted with ethyl acetate. The extract solution is washed with water, dried and evaporated to remove the solvent to give 2β-chloromethyl-2α-methyl-6β-phenoxyacetamidopenam-3α-carboxylic acid (193 mg).

EXAMPLE VI-4.

A mixture of benzhydryl 7β-(α-tert.-butoxycarbonylamino-α-phenylacetamido)-3β-chloro-3α- methylcepham-4α-carboxylate (150 mg), trifluoroacetic acid (4 ml), and anisole (1 ml) is stirred at room temperature for 30 minutes, then evaporated in vacuo, The residue is treated with ether to remove soluble material. The insoluble material is 7β-(α-aminophenylacetamido)- 3β-chloro-3α-methylcepham-4α-carboxylic acid trifluoroacetate. The material is mixed with water (1.5 ml) and 25% Amberlite LA-1$^R$ is methyl isobutyl ketone (1.5 ml), and stirred for 2 hours to give an insoluble material which is collected by filtration. The solid is washed with water, methyl isobutyl ketone, and ethyl acetate, and dried to give 7β-(α-aminophenylacetamido)-3β-chloro-3α-methylcepham-4α-carboxylic acid (35 mg). Yield: 40%. IR: $\nu_{max}^{Nujol}$ 5.8, 5.7, 5.7μ.

EXAMPLE IV-5.

A mixture of 2,2,2-trichloroethyl 3β-chloro-3α-methyl-7β-(5-methyl-3-phenylisoxazol-4-carboxamido)cepham-4α-carboxylate (210 mg), zinc metal (250 mg), and acetic acid (3 ml) is stirred at room temperature for 3 hours. The reaction mixture is filtered to remove solid, and the filtrate is evaporated to give a residue, which is dissolved in ethyl acetate and washed with aqueous sodium hydrogen carbonate. The water layer is acidified with hydrochloric acid and extracted with ethyl acetate. The extract solution is washed with water, dried, and evaporated to give 3β-chloro-3α-methyl-7β-(5-methyl-3-phenylisoxazol-4-carboxamido)cepham-4α-carboxylic acid (89 mg). m.p. 210°C.

EXAMPLE VI-6.

A mixture of benzhydryl 3β-chloro-3α-methyl-7β(2-ketopinoylamino)-cepham-4α-carboxylate (80 mg), anisole (0.1 ml), trifluoroacetic acid (0.1 ml), and methylene chloride (1 ml) is kept at 0°C for 5 minutes then at room temperature for 1 hour. The reaction mixture is evaporated, and the residue is dissolved in a mixture of water and ethyl acetate. The ethyl acetate layer is extracted with sodium hydrogen carbonate. The extract solution is covered with ethyl acetate, and aciddified with 10% hydrochloric acid. The ethyl acetate layer is dried over sodium sulfate and evaporated to give 49 mg 3β-chloro-3α-methyl-7β-(2-ketopinoylamino)-cepham-4α-carboxylic acid.

EXAMPLE VI-7.

To a solution of 2,2,2-trichloroethyl 6β-phenoxyacetamido-2β-chloromethyl-2α-methylpenam-3α-carboxylate (400 mg) in N,N-dimethylformamide (8 ml) and acetic acid (1.6 ml) is added under ice cooling zinc powder (272 mg), and the mixture is stirred for 1.5 hours. After the solid material being filtered off, the solution is washed with water and dried over sodium sulfate. The dried solution is evaporated in high vacuum to give crude 6β-phenoxyacetamido-2β-chloromethyl-2α-methylpenam-3α-carboxylic acid (260 mg). IR: $\nu_{max}^{CHCl_3}$ 3440, 1780, 1730, 1695 cm$^{-1}$.

The methyl ester of this acid prepared by the action of diazomethane in ether, is identical with the authentic sample prepared by another method.

EXAMPLE VII-1.

A solution of methyl 6β-amino-2β-chloromethyl-2α-methylpenam-3α-carboxylate (266 mg) and N-carbethoxyphthalimide (218 mg) in dioxane (5 ml) is stirred for 20 minutes at room temperature. The reaction mixture is poured into water and extracted with ethyl acetate. The extract solution is washed with water, dried, and evaporated to give methyl 2β-chloro-methyl-2α-methyl-6β-phthalimidopenam-3α-carboxylate (320 mg). yield: 81%.

EXAMPLE VII-2.

A solution of benzhydryl 6β-amino-2β-chloromethyl 2α-methylpenam-3α-carboxylate (840 mg), thiopheneacetic acid (283 mg), and N,N-dicyclohexylcarbodiimide (450 mg) in dioxane (10 ml) is kept at room temperature for 1 hour. The reaction mixture is filtered, and the filter is concentrated. The residue is treated with a mixture of ether and petroleum ether to give benzhydryl 2β-chloromethyl-2α-methyl-6β-thienyl-acetamidopenam-3α-carboxylate (834 mg) Yield: 77%. IR: $\nu_{max}^{CHCl_3}$ 5.9, 5.6, 5.7μ. NMR: $\delta^{CDCl_3}$ 3.4, 1.4.

EXAMPLE VII-3.

To a solution of phenylacetic acid (136 mg) and p-nitrophenol (152 mg) in tetrahydrofuran (2 ml) is added dropwise a solution of N,N-dicyclohexylcarbodiimide (226 mg) in tertrahydrofuran (2 ml) under ice cooling. After 1 hour's stirring, the reaction mixture is filtered, and the filtrate is evaporated to dryness in vacuo. The residue is dissolved in methylene chloride (8 ml), and mixed with a solution of benzhydryl 6β-amino-2β-chloromethyl-2α-methylpenam-3α-carboxylate (362 mg) in methylene chloride (10 ml). After being kept at room temperature overnight, the mixture is filtered, and the filtrate is washed with 5% aqueous sodium hydrogen carbonate and water, dried, and evaporated. Treatment of the residue with a mixture of ether and petroleum ether gives benzhydryl 6β-phenylacetamido-2β-chloromethyl-2α-methylpenam-3α-carboxylate (311 mg). Yield: 60%.

EXAMPLE VII-4.

A mixture of 7β-amino-3β-chloro-3α-methylcepham-4α-carboxylic acid (150 mg), chloroform (1 ml), and triethylamine (0.2 ml) is stirred under ice cooling for 1 hour. To this solution is added dropwise a solution of benzoyl chloride (84 mg) in chloroform (1 ml) and the mixture is stirred at room temperature for 2 hours. The reaction mixture is adjusted to pH 1.5 – 2 with diluted hydrochloric acid, and extracted with methylene chloride. The extract solution is adjusted to pH 8 with diluted sodium hydroxide, shaken, and the water layer is separated and washed with ether. The water layer is evaporated at a temperature lower than 30°C to give sodium 7β-benzoylamino-3β-chloro-3α-methylcepham-4α-carboxylate (127 mg). Yield: 56%.

EXAMPLE VII-5.

To a cooled solution of α-tert.-butoxycarbonylaminophenylacetic acid (1.0 g) and triethylamine (405 mg) in tetrahydrofuran (16 ml), is added isobutylchloroformate (550 mg) at −10°C and the mixture is stirred for 10 minutes. To the solution is added a solution of 7β-amino-3β-chloro-3α-methylcepham-4α-carboxylic acid (870 mg), and triethylamine (405 mg) in a mixture of tetrahydrofuran and water (1:1; 15 ml), and the mixture is stirred for 1 hour at 5°C, and for 1 hour at room temperature. The reaction mixture is evaporated in vacuo to remove tetrahydrofuran, and the resultant solution is diluted with a mixture of water and ethyl acetate (3:1). The aqueous layer is separated, acidified to pH 3 with 10% hydrochloric acid, and extracted with ethyl acetate. The extract solution is washed with water, dried, and evaporated to give 7β-(α-tert.-butoxycarbonylaminophenylacetamido)-3β-chloro-3α-methylcepham-4α-carboxylic acid (1.5 g). Yield: 77%.

EXAMPLE VII-6.

To a solution of benzhydryl 7β-amino-3β-chloro-3α-methylcepham-4α-carboxylate (209 mg) in methylene chloride (3 ml) is added triethylamine (56 mg), and the mixture is mixed with a solution of phenoxyacetyl chloride (79 mg) in methylene chloride (2 ml) under ice cooling. After being left to stand for 2 hours, the mixture is washed successively with dilute hydrochloric acid, 5% aqueous sodium hydrogen carbonate, and water, then dried, and evaporated in vacuo. Recrystallization of the residue with a mixture of ether and petroleum ether gives benzhydryl 3β-chloro-3α-methyl-7β-phenoxyacetamidocepham-4α-carboxylate (220 mg). Yield: 82%.

EXAMPLE VIII-1.

To a solution of 2β-chloromethyl-2α-methyl-6β-phenoxyacetamidopenam-3α-carboxylic acid (2.2 g) in tetrahydrofuran (20 ml) is added dropwise pyridine (0.45 g) and a solution of 2,2,2-trichloroethyl chloroformate (1.2 g) in tetrahydrofuran (10 ml). The reaction mixture is kept at room temperature overnight, then evaporated in vacuo to remove the solvent. The residue is dissolved in ethyl acetate, and the solution is washed with 5% aqueous sodium hydrogen carbonate and water, dried, and evaporated. The residue (2.8 g) is 2,2,2-trichloroethyl 2β-chloromethyl-2α-methyl-6β-phenoxyacetamidopenam-3α-carboxylate. Yield: 95%.

EXAMPLE VIII-2.

To a solution of 2β-chloromethyl-2α-methyl-6β-phenoxyacetamidopenam-3α-carboxylic acid (3.0 g) and p-bromophenacyl bromide (2.62 g) in dimethylformamide (30 ml) is added triethylamine (8.0 g), and the mixture is stirred for 3 hours. The reaction mixture is diluted with iced water, and separated crystals are collected by filtration, and dried to give p-bromophenacyl 2β-chloromethyl-2α-methyl-6β-phenoxyacetamidopenam-3α-carboxylate (3.82 g). Yield: 84%.

EXAMPLE VIII-3.

To a solution of 3β-chloro-3α-methyl-7β-(α-tert.-butoxycarbonylaminophenylacetamido)cepham-4α-carboxylic acid (0.9 g) in methylene chloride (20 ml), is added a solution of diphenyldiazomethane in methylene chloride until the red color or the reaction solution does not disappear. The reaction mixture is evaporated to remove the solvent, leaving a residue of benzhydryl 3β-chloro-3α-methyl-7β-phenylacetamidocepham-4α-carboxylate (1.17 g). Yield: 96%.

EXAMPLE VIII-4.

To a solution of 3β-chloro-3α-methyl-7β-phenylacetamidocepham-4α-carboxylic acid (3.7 g) in acetone (30 ml) is added at −5°C a solution of pyridine (1 drop) in ethyl chloroformate (0.96 g), and the mixture is left standing for 30 minutes. To this mixture is added benzaldoxime (1.2 g) in acetone (10 ml), and the mixtures is stirred at room temperature for 2 hours. The reaction mixture is filtered through silica gel layer, and the filtrate is concentrated in vacuo. A solution of the residue in ethyl acetate is washed with 1% aqueous sodium hydrogen carbonate and water, dried, and concentrated. Treatment of the residue with ether gives the benzaldoxime-O-ester of 3β-chloro-3α-methyl-7β-phenylacetamidocepham-4α-carboxylic acid. Yield: 68.5%.

EXAMPLE VIII-5.

A solution of 3β-chloro-3α-methyl-7β-phenoxyacetamidocepham-4α-carboxylic acid (2.74 g), p-nitrobenzyl bromide (1.52 g), and triethylamine (1 ml) in dimethylformamide (30 ml) is kept at room temperature for 3 hours. The reaction mixture is poured into ice water, and extracted with ethyl acetate. The extract solution is washed with water, dried, and evaporated in vacuo to give p-nitrobenzyl 3β-chloro-3α-methyl-7β-phenoxyacetamidocepham-4α-carboxylate (3.45 g). Yield: 93%.

What we claim is:

1. A process for the preparation of a 2'-halopenicillin compound of the following formula:

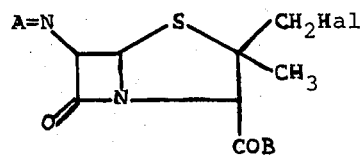

wherein A=N is a substituted amino selected from the group consisting of phenoxyacetamido, phenylacetamido, thienylacetamido, phenylglycylamino, phenylglycylamino substituted by alkanoyl or alkoxycarbonyl having up to 12 carbon atoms on its amino group, 2-ketopinoylamino, norbornanecarbonylamino, benzamido, 3-phenyl-5-methylisoxazole-4-carbonamido, alkoxycarbonamido having up to 12 carbon atoms, haloalkoxycarbonamido having up to 12 carbon atoms, o-nitrophenylsulfenylamino, benzylideneamino, hydroxybenzylideneamino, phthalimido, 2,2-dimethyl-4-phenyl-5-oxoimidazolidin-1-yl, 2,2-dimethyl-3-nitroso-4-phenyl-5-oxoimidazolidin-1-yl, and tritylamino; B is a member selected from the group consisting of alkoxy having 1 to 12 carbon atoms, haloalkoxy having 1 to 12 carbon atoms, phenacyloxy, halophenacyloxy, methoxymethoxy, alkanoyloxymethoxy having up to 12 carbon atoms, benzyloxy, benzyloxy substituted by nitro, alkoxy having up to 12 carbon atoms or halo, benzhydryloxy, benzalamino-oxy, hydroxy, sodio-oxy, potassio-oxy, trimethylsilyloxy, trimethyltin-oxy, and triethylammonium-oxy; and Hal is fluorine, chlorine, bromine or iodine, by the reaction of a penicillin-1-oxide compound of the following formula:

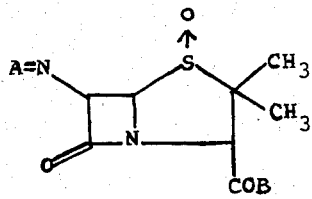

wherein A and B are as defined above, with an acid halide selected from the group consisting of alkanoyl halides having 1 to 12 carbon atoms, chloroacetyl chloride, oxalyl halide, crotonyl halide, ethynylacetyl halide, phenylacetyl halide, thiopheneacetyl halide, benzoyl halide, benzoyl halide substituted by nitro, methoxy, alkyl having 1 to 12 carbon atoms or halogen, naphthoyl halide, thienoyl halide, nicotinoyl halide, quinolinecarbonyl halide, alkanesulfonyl halide having up to 12 carbon atoms, benzenesulfonyl halide, benzenesulfonyl halide substituted by alkyl having 1 to 12 carbon atoms, methoxy, nitro or halo, naphthalenesulfonyl halide, quinoline-8-sulfonyl halide, 1,3,4-thiadiazolylsulfonyl halide, alkyl haloformate having up to 12 carbon atoms, and phenyl haloformate, in the presence of a base selected from the group consisting of dialkylamine or trialkylamine having up to 12 carbon atoms, N-methylpiperidine, N-methylmorpholine, N-ethylpyrrolidine, N,N-dimethylbenzylamine, pyridine, picoline, lutidine, quinoline, isoquinoline, N,N-dimethylaniline, urea, thiourea, guanidine, and N-lower alkylurea having up to 12 carbon atoms, at a temperature of from 70°C to 130°C.

2. A process according to claim 1, wherein the acid halide is acetyl chloride, propionyl chloride, pivaloyl chloride, oxalyl chloride, benzoyl fluoride, benzoyl chloride, benzoyl bromide, p-nitrobenzoyl chloride, p-anisoyl chloride, toluene-p-sulfonyl chloride, methanesulfonyl chloride, or ethyl chloroformate.

3. A process according to claim 1, wherein the base is pyridine, picoline, lutidine, triethylamine, or trimethylamine.

4. A process according to claim 1, wherein the reaction is carried out at a temperature in the range from 80°C to 120°C.

5. A process according to claim 1, wherein one to ten mole equivalents, or one to two mole equivalents of the acid halide are used for one mole equivalent of the penicillin-1-oxide compound.

6. A process according to claim 1, wherein the reaction is carried out in a solvent selected from benzene, toluene, dioxane, and N,N-dimethylformamide.

7. A process according to claim 1, wherein the acid halide and the base are initially mixed to form an onium salt adduct, which is used in place of the two reagents.

* * * * *